United States Patent
Walter et al.

(10) Patent No.: US 8,673,002 B2
(45) Date of Patent: *Mar. 18, 2014

(54) MEDICAL TOOLS FOR FACILITATING KERATOPLASTY AND RELATED METHODS

(71) Applicant: Wake Forest University Health Sciences, Winston-Salem, NC (US)

(72) Inventors: Keith Andrew Walter, Winston-Salem, NC (US); Kurt Weber, Winston-Salem, NC (US)

(73) Assignee: Wake Forest University Health Science, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/901,115

(22) Filed: May 23, 2013

(65) Prior Publication Data
US 2013/0253529 A1   Sep. 26, 2013

Related U.S. Application Data

(63) Continuation of application No. 11/626,959, filed on Jan. 25, 2007, now Pat. No. 8,470,029.

(60) Provisional application No. 60/762,452, filed on Jan. 26, 2006, provisional application No. 60/788,221, filed on Mar. 31, 2006, provisional application No. 60/865,045, filed on Nov. 9, 2006.

(51) Int. Cl.
*A61F 2/16* (2006.01)

(52) U.S. Cl.
USPC .................................................. 623/6.12

(58) Field of Classification Search
USPC ............... 606/107, 166; 623/5.11, 6.11, 6.12
See application file for complete search history.

(56) References Cited

U.S. PATENT DOCUMENTS

| | | | |
|---|---|---|---|
| 4,573,998 | A | 3/1986 | Mazzocco |
| 4,619,256 | A | 10/1986 | Horn |
| 4,681,102 | A | 7/1987 | Bartell |
| 4,834,094 | A | 5/1989 | Patton et al. |
| 4,836,201 | A | 6/1989 | Patton et al. |
| 4,880,000 | A | 11/1989 | Holmes et al. |
| 4,919,130 | A | 4/1990 | Stoy et al. |
| 4,934,363 | A | 6/1990 | Smith et al. |
| 4,955,889 | A | 9/1990 | Van Gent |
| 4,994,079 | A | 2/1991 | Genese et al. |

(Continued)

FOREIGN PATENT DOCUMENTS

| | | |
|---|---|---|
| JP | 2001 008954 | 1/2001 |
| WO | WO 96/26759 | 9/1996 |
| WO | WO 2006/113474 | 10/2006 |
| WO | WO 2007/089508 | 8/2007 |

OTHER PUBLICATIONS

John, Stitchless Corneal Transplantation, Cataract & Refractive Surgery Today, pp. 27-30, 2004.

(Continued)

*Primary Examiner* — Ryan Severson
*Assistant Examiner* — Jonathan W Miles
(74) *Attorney, Agent, or Firm* — Myers Bigel Sibley & Sajovec, P.A.

(57) ABSTRACT

Systems, devices and methods for performing small incision DLEK include providing a corneal transplantation donor tissue graft; then forming the tissue graft into an implantable configuration using the flexible substrate. Related medical kits and tools for forming a compact or rolled donor tissue graft are also described.

19 Claims, 24 Drawing Sheets

(56) References Cited

U.S. PATENT DOCUMENTS

| | | |
|---|---|---|
| 5,098,439 A | 3/1992 | Hill et al. |
| 5,443,473 A | 8/1995 | Miller et al. |
| 5,496,339 A | 3/1996 | Koepnick |
| 5,860,984 A | 1/1999 | Chambers et al. |
| 5,876,440 A | 3/1999 | Feingold |
| 5,947,975 A | 9/1999 | Kikuchi et al. |
| 6,387,101 B1 | 5/2002 | Butts et al. |
| 6,921,415 B2 | 7/2005 | Callahan et al. |
| 7,828,844 B2 | 11/2010 | Marmo et al. |
| 2002/0055753 A1 | 5/2002 | Silvestrini |
| 2003/0018347 A1 | 1/2003 | Pallikaris et al. |
| 2003/0078487 A1 | 4/2003 | Jeffries et al. |
| 2004/0238392 A1 | 12/2004 | Peterson et al. |
| 2005/0010244 A1 | 1/2005 | Mells |
| 2005/0033308 A1 | 2/2005 | Callahan et al. |
| 2005/0246016 A1 | 11/2005 | Miller et al. |
| 2005/0288696 A1 | 12/2005 | Pallikaris et al. |
| 2006/0020267 A1 | 1/2006 | Marmo |
| 2006/0235430 A1 | 10/2006 | Le et al. |
| 2010/0274257 A1 | 10/2010 | Neusidl et al. |

OTHER PUBLICATIONS

Terry et al., Small-Incision Deep Lamellar Endothelial Keratoplasty (DLEK), Six-Month Results in the First Prospective Clinical Study, Cornea, 2005, pp. 59-65, vol. 24, No. 1.

International Search Report and Written Opinion for corresponding PCT Application No. PCT/US2007/01932, Date of Mailing Jan. 7, 2008.

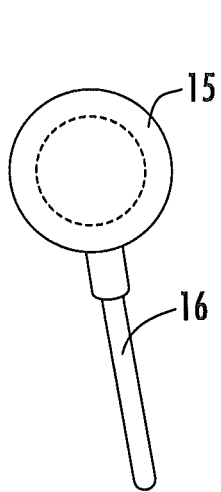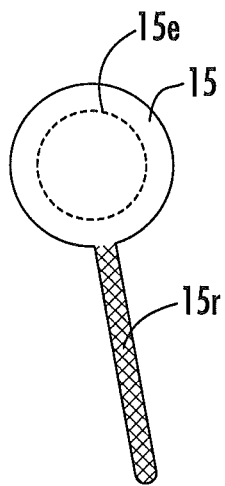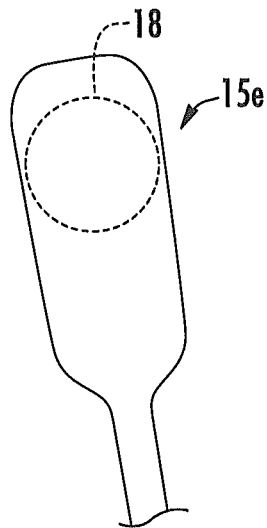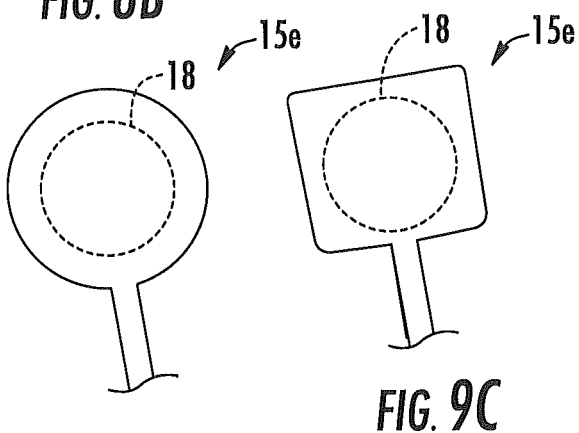
FIG. 8A  FIG. 8B  FIG. 9A  FIG. 9B  FIG. 9C

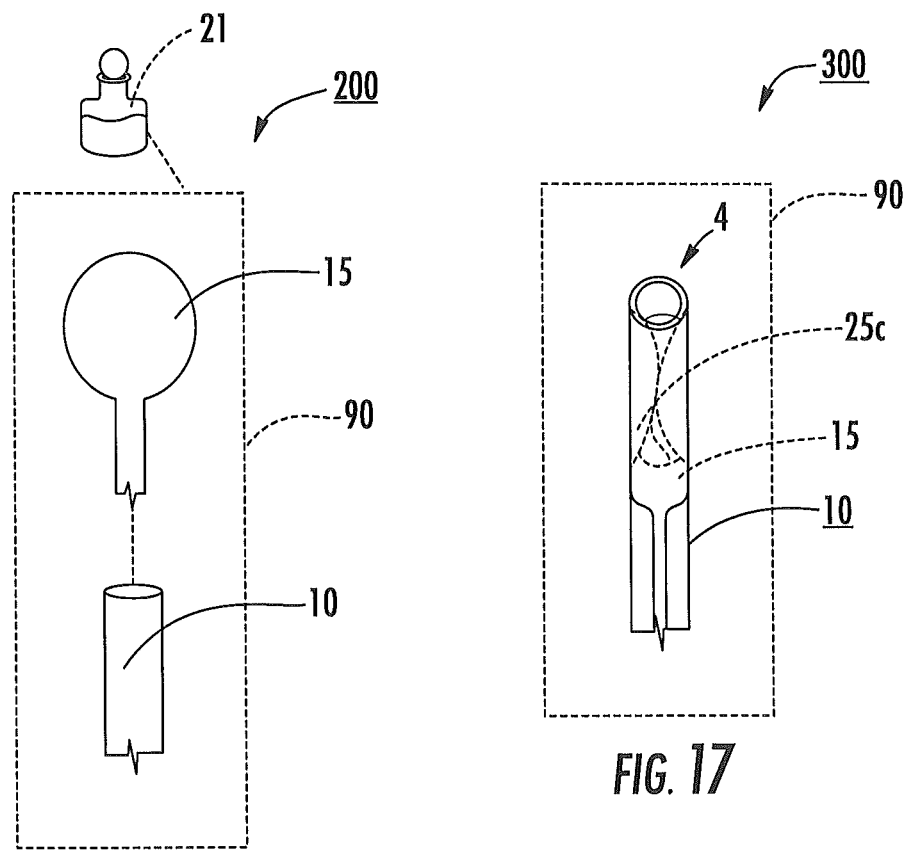
FIG. 16
FIG. 17
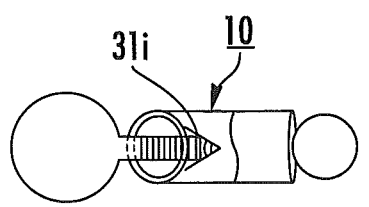
FIG. 18A
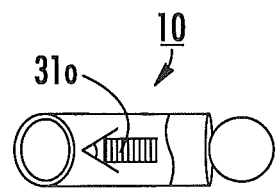
FIG. 18B

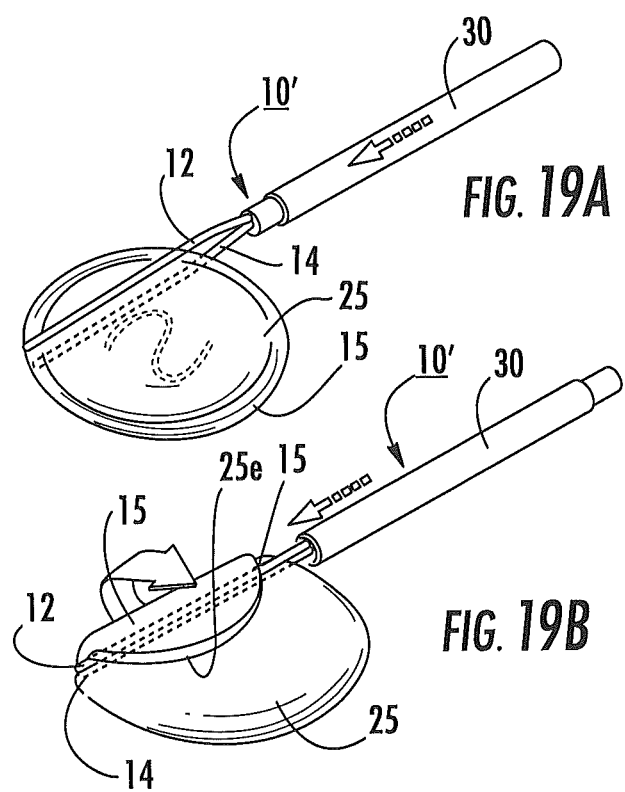

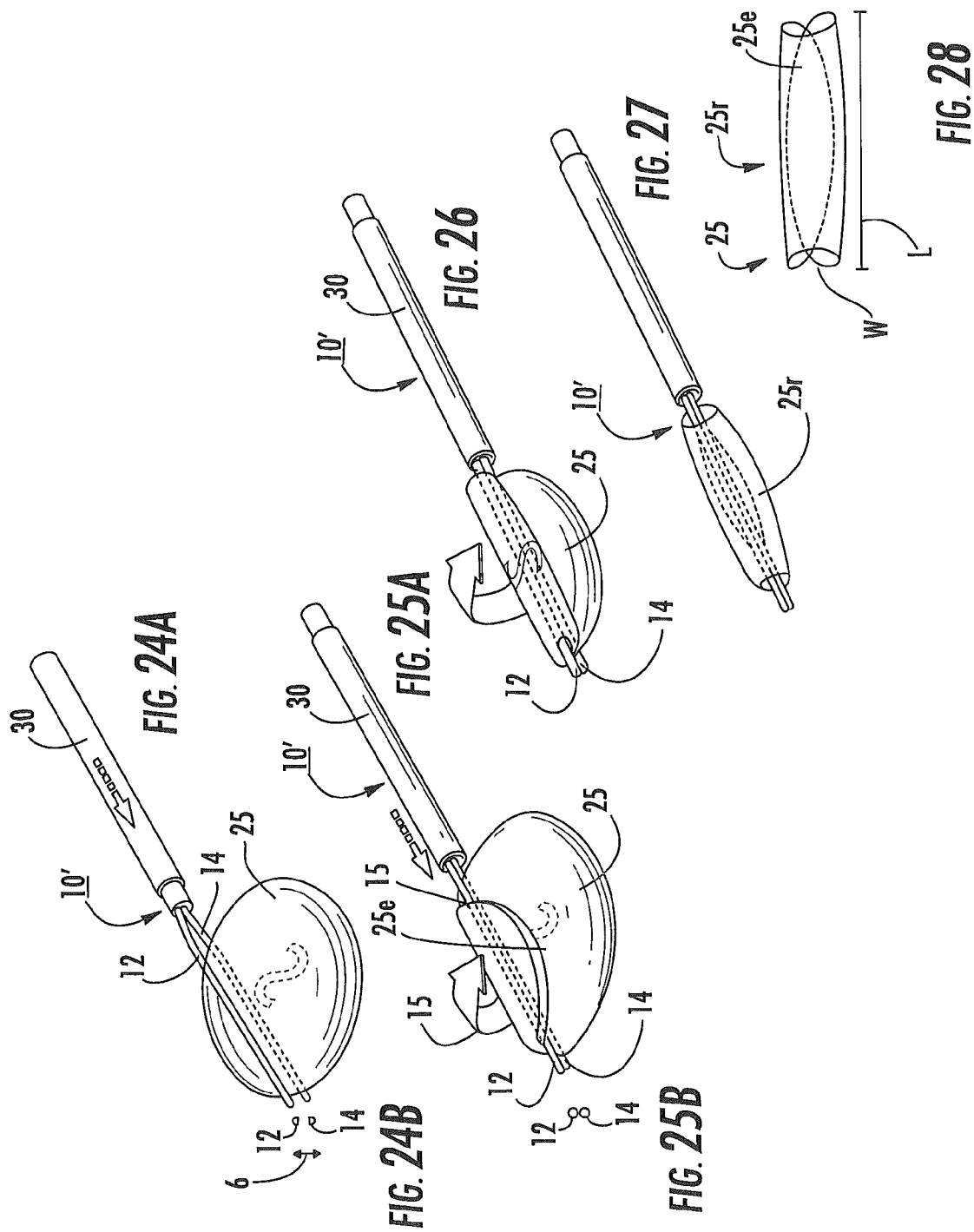

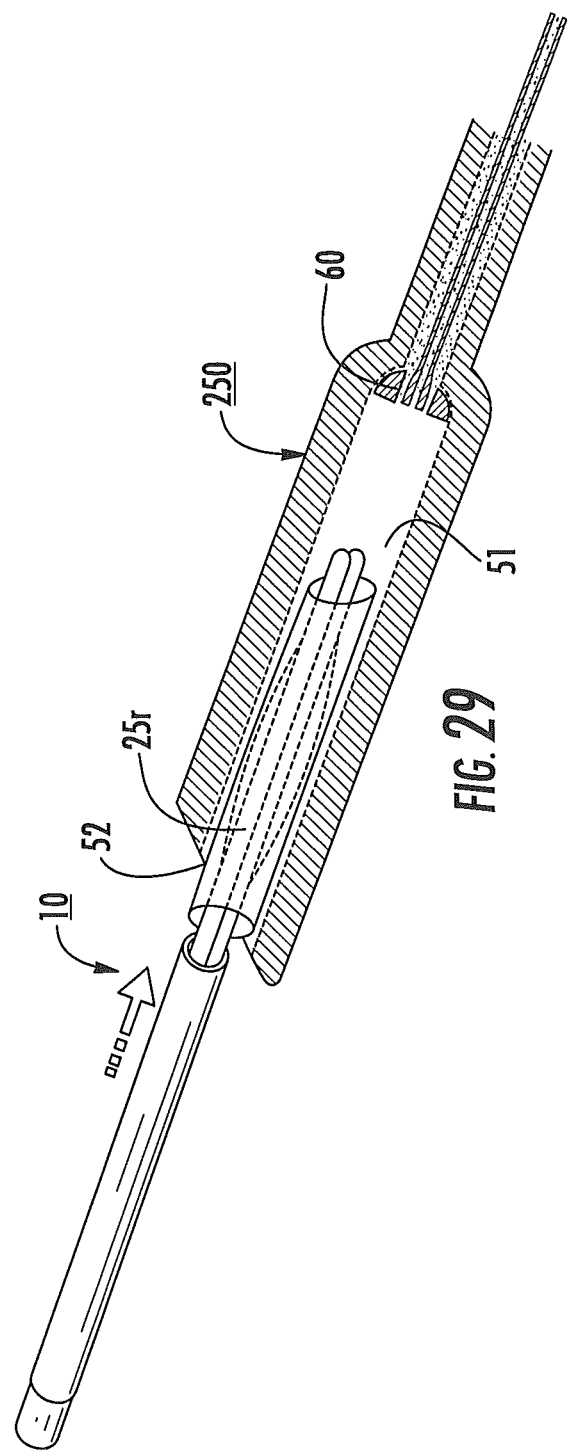

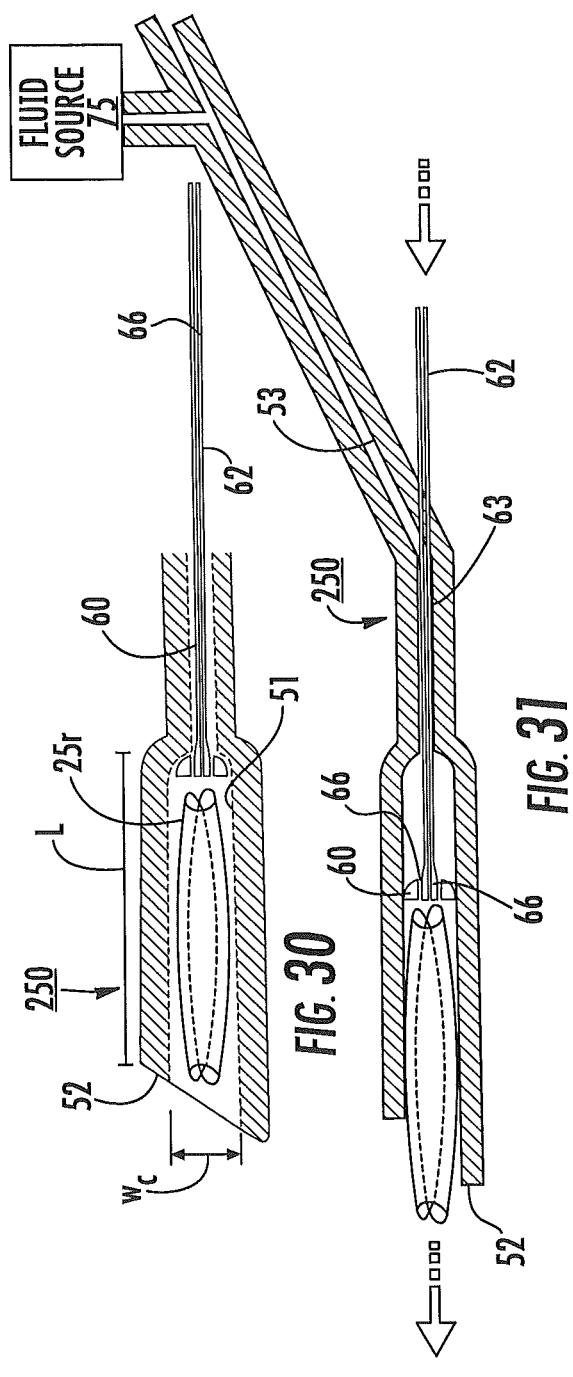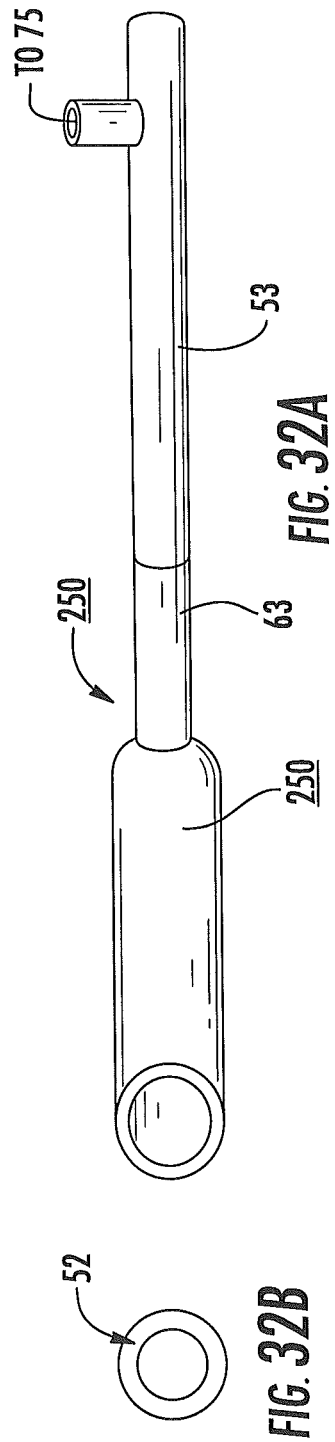

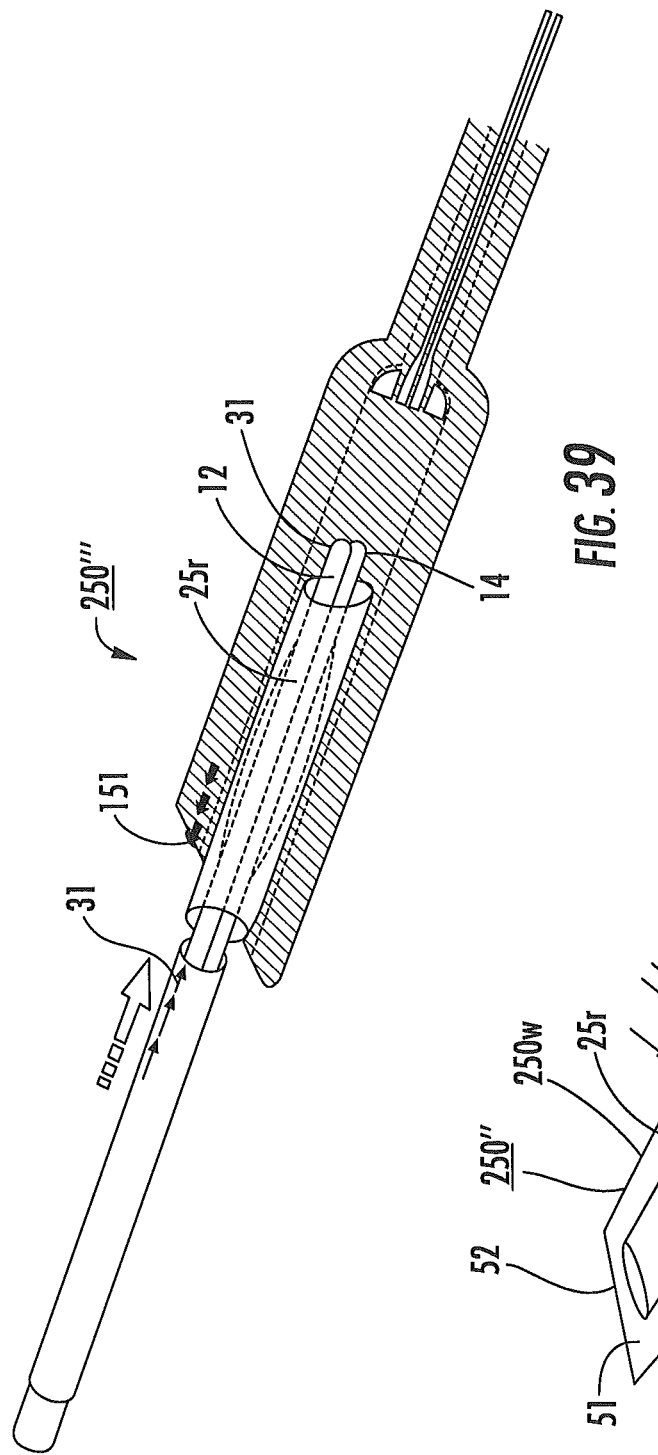
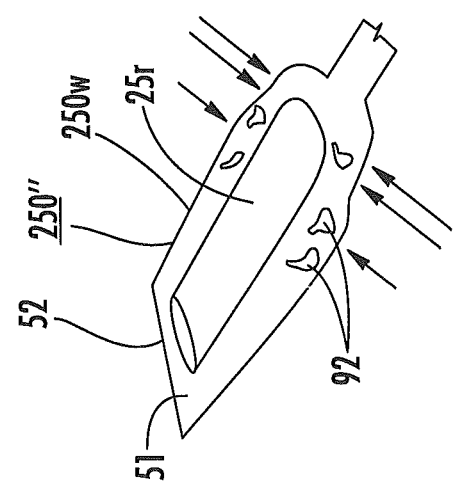
FIG. 38
FIG. 39

MEDICAL TOOLS FOR FACILITATING KERATOPLASTY AND RELATED METHODS

RELATED APPLICATIONS

This application is a continuation of U.S. patent application Ser. No. 11/626,959, filed Jan. 25, 2007, which claims the benefit of priority of U.S. Provisional Application Ser. No. 60/762,452, filed Jan. 26, 2006, U.S. Provisional Application Ser. No. 60/788,221, filed Mar. 31, 2006, and U.S. Provisional Application Ser. No. 60/865,045, filed Nov. 9, 2006, the contents of which are hereby incorporated by reference as if recited in full herein.

FIELD OF THE INVENTION

The invention relates to tools that facilitate corneal surgeries to implant donor tissue.

BACKGROUND OF THE INVENTION

Conventional corneal transplantation surgery, also known as penetrating keratoplasty, uses full-thickness corneal replacement with sutures. Recently, deep lamellar endothelial keratoplasty (DLEK) has been used to place a partial-thickness corneal replacement from a healthy donor cornea into a host/recipient along with its endothelium. DLEK is also known as "stitchless" corneal transplantation.

Some researchers and physicians believe that DLEK is a major advance in the way that diseased human cornea is replaced with healthy donor corneal endothelium. An exemplary transplantation procedure of a conventional donor harvesting and recipient preparation is described in Thomas John, *Stitchless Corneal Transplantation*, Cataract & Refractive Surgery Today, pp. 27-30, August 2004. As described, a donor corneal endothelium is coated with viscoelastic material and the cornea and its attached scleral rim are placed in an artificial chamber. After excision of the anterior stromal disc, the donor corneal stroma can be flipped on itself so that the donor corneal stroma rests on a Teflon® block with the stromal side facing down and is held in place via vacuum. Trephination can be carried using a MORIA trephine. The deep stromal-endothelia donor disc can be carefully placed onto a viscoelastic-coated Ousley spatula (available from Bausch & Lomb) with the endothelial side facing down.

More recently, a smaller incision DLEK technique has been proposed in which the donor disc (usually between about 8-8.25 mm in diameter) can be held by simple forceps. In this procedure, the surgeon folds the transplant in half (endothelial side down) and inserts the transplant material through a 5 mm incision into the host anterior chamber (under air) and onto the host bed of the pre-resected central area. Instrastromal Cindy scissors can be used in a free hand manner to excise the recipient disc using about an 8 mm circular ink mark on an epithelial surface as a visual template. A separate tool is typically used to manipulate the tissue into position. Once in the anterior chamber, the folded donor disc is irrigated with saline to remove viscoelastic material, opened further with an air bubble (which can be decreased in size), then rolled over the air bubble, thereby placing the donor stromal surface into contact with the recipient stromal bed for self-adhesion. Staining of the donor disc can help a surgeon properly align the disc in the host bed. A reverse Sinskey hook can be used for final positioning to tuck the donor edges anterior to the recipient bed edges to inhibit later dislodgement. See, Terry et al., *Small Incision Deep Lamellar Endothelial Keratoplasty (DLEK) Six Month Results in the First Prospective Clinical Study*, Cornea, Volume 24, No. 1, pp. 59-65, January 2005.

Despite the foregoing, there is a need to provide surgical instruments that can facilitate DLEK or stitchless corneal transplantation.

SUMMARY OF EMBODIMENTS OF THE INVENTION

Embodiments of the present invention are directed to devices and methods that can facilitate small incision DLEK and/or stitchless corneal transplantation.

Some embodiments are directed to methods of configuring a deep stromal endothelial donor corneal disc (graft) for transplantation. The methods include: (a) providing a corneal transplantation donor disc; and (b) roiling the disc into a compact implant configuration.

In some methods, the donor disk may have a diameter of between about 8 mm to about 8.25 mm. The donor disc compact configuration may have a cross-sectional width that is less than about 3 mm (for example, about 2.5 mm) suitable for entering a scleral access incision sized at less than about 4 mm (for example, about 3 mm).

In particular embodiments, the provided corneal donor disc has a first unrolled generally planar configuration and the method can include: (a) providing a rolling tool having first and second cooperating members that define a gap space therebetween; (b) inserting a portion of the planar donor disc between the first and second cooperating members; (c) forcing the first and second members together to trap a portion of the donor disc therebetween; then (d) rotating the rolling tool to roll the donor disc about itself.

Other embodiments are directed to surgical transplant donor corneal disc kits. The kits include a rolled partial thickness donor corneal transplant disc held in a sterilized package.

Yet other embodiments are directed to systems for performing small incision DLEK. The systems include: (a) a rolled donor graft disc for endothelial replacement surgery; and (b) a rolled disc delivery device for releasably holding the rolled disc for surgical introduction in a recipient stromal bed via a small incision access site.

Some embodiments are directed to methods of configuring a deep stromal endothelial donor corneal tissue graft for transplantation. The methods include: (a) providing a corneal transplantation donor tissue graft; (b) optionally placing the donor tissue graft on a flexible substrate; and (c) forming the donor tissue graft into a compact implantable configuration using the flexible substrate.

In some methods, the donor disk may have a diameter of between about 8 mm to about 9 mm. The donor disc compact configuration may have a cross-sectional width that is less than about 3 mm (for example, about 2.5 mm) suitable for entering a scleral access incision sized at less than about 4 mm (for example, about 3 mm).

Some embodiments are directed to surgical transplant donor corneal disc kits that include a rolled partial thickness donor corneal transplant disc held on a flexible substrate in a sterilized package.

In some embodiments, the kit can include a lubricant material disposed about the rolled disc and the kit may also include a disc-holding member configured to releasably hold the rolled disc.

Other embodiments are directed to corneal donor disc medical tools that include: (a) a holding member with a holding chamber having a wall; and (b) a flexible substrate in cooperating relationship with the holding chamber. The flexible substrate is configured to slidably enter the holding chamber and hold a corneal donor tissue graft in the holding chamber in a rolled configuration.

The flexible substrate and/or the holding chamber can be configured to inhibit rotation of the tissue graft in the chamber so that a user can control orientation of the stroma and endothelial sides of the implant. The tool can be single-use disposable.

Some embodiments are directed to donor harvesting tool kits that optionally include a flexible substrate. The kit holds a donor corneal grafting disc in a rolled configuration for small incision DLEK. The donor disc can have a diameter between about 8-9 mm and a thickness between about 100-200 μm.

Still other embodiments are directed to medical products with a rolled donor corneal disc held on a flexible substrate for performing a small incision DLEK.

Some embodiments are directed to systems for use in small incision DLEK. The systems include: (a) a rolled donor graft disc for endothelial replacement surgery; and (b) a rolled disc delivery device for releasably holding the rolled disc for surgical introduction in a recipient stromal bed via a small incision access site.

Some embodiments are directed to donor harvesting tools configured to releasably engage and form a donor corneal grafting disc having a diameter between about 8-9 mm and a thickness between about 100-200 μm (typically about 150 μm) into a rolled configuration for small incision "stitchless" or self-healing DLEK. The harvesting tool can also be used as the implantation tool (i.e., a dual-use single device). The donor disk may be held on a flexible substrate during surgical delivery.

Other embodiments are directed to methods for delivering donor tissue to an implantation site. The methods include: (a) holding the donor tissue in a rolled configuration on a flexible substrate in a cannula; (b) positioning the cannula at the target implantation site; then (c) slidably retracting the cannula and the flexible substrate away from the implantation site, thereby releasing the donor tissue at the implantation site.

Additional embodiments are directed to other methods for delivering donor tissue to an implantation site. The methods include: (a) holding the donor tissue in a rolled configuration in a cannula; (b) positioning the cannula at the implantation site; then (c) pushing the donor tissue out of the cannula (typically by contact with a pushing member and/or fluid), thereby releasing the donor tissue proximate the implantation site.

It is noted that any of the features claimed with respect to one type of claim, such as a system, apparatus, or computer program, may be claimed or carried out as any of the other types of claimed operations or features.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIGS. 8A and 8B are partial top views of exemplary flexible substrate configurations with releasable and integral arms, respectively, according to embodiments of the present invention.

FIGS. 9A-9C are top schematic views of exemplary flexible substrate configurations according to embodiments of the present invention.

FIG. 16 is a schematic illustration of an exemplary donor harvest medical kit according to embodiments of the present invention.

FIG. 17 is a schematic illustration of an exemplary medical kit with a rolled donor disc preformed and ready for implantation according to other embodiments of the present invention.

FIGS. 18A and 18B are partial top views of the device shown in FIG. 1A illustrating that the device may include visual orientation and/or alignment indicia according to embodiments of the present invention.

FIGS. 19A and 19B are perspective views of a flexible substrate showing that the flexible substrate can be used to hold the donor tissue graft with other medical tool configurations according to embodiments of the present invention.

FIG. 24A is a side perspective view of a medical rolling tool according to embodiments of the present invention.

FIG. 24B is an end view of the device shown in FIG. 24A illustrating a gap space between upper and lower members according to some embodiments of the present invention.

FIG. 25A is a side perspective view of the device shown in FIG. 24A illustrating the device rolling a donor disc according to embodiments of the present invention.

FIG. 25B is an end view of the device shown in FIG. 25A, illustrating the upper and lower members abutting each other according to some embodiments of the present invention.

FIGS. 26 and 27 are side perspective views of the device shown in FIGS. 24A and 25A illustrating a sequence of operations used to roll the disc into a surgical preparation form according to embodiments of the present invention.

FIG. 28 is a side view of an exemplary surgical rolled donor disc according to embodiments of the present invention.

FIG. 29 is a side perspective partial cutaway view of the tool and rolled disc of FIG. 27 being placed in a surgical delivery tool according to some embodiments of the present invention.

FIG. 30 is a side partial cutaway view of the tool shown in FIG. 29 illustrating the rolled donor disc held therein according to embodiments of the present invention.

FIG. 31 is a side partial cutaway view of the tool shown in FIG. 30 illustrating the donor disc being expelled from the chamber of the delivery device according to some embodiments of the present invention.

FIG. 32A is a top view of the device shown in FIG. 31.

FIG. 32B is an end view of the device shown in FIG. 32A.

FIG. 38 is a side cutaway view of another delivery device for a rolled disc according to other embodiments of the present invention.

FIG. 39 is a side perspective partial cutaway view of the device shown in FIG. 29 illustrating that visual alignment indicia may be used according to embodiments of the present invention.

DETAILED DESCRIPTION

Figure 1A:
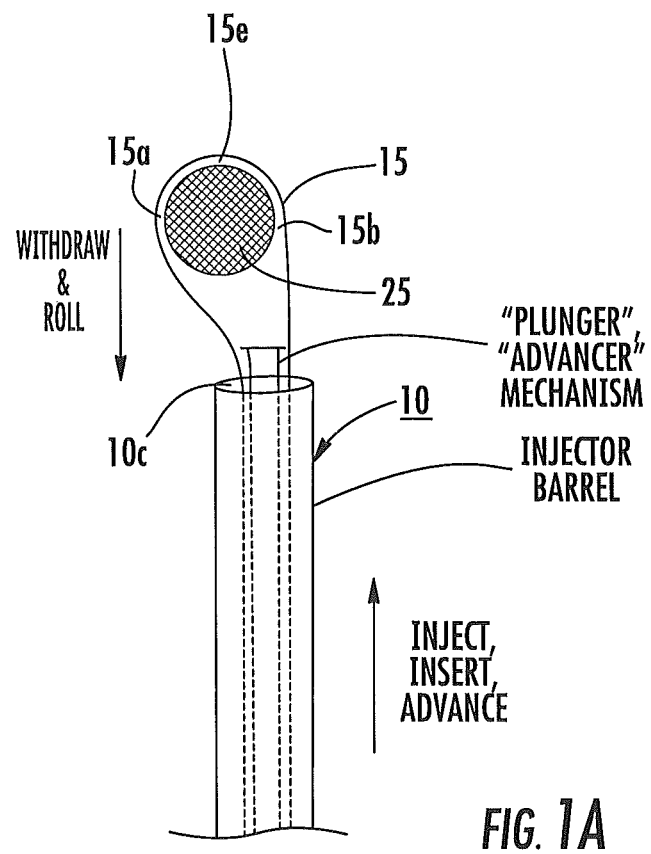
FIG. 1A is a schematic illustration of a medical tool according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. Features described or shown with respect to one embodiment may be used with a different embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "rolled" and derivatives thereof refer to turning or coiling the donor tissue about an axis into a substantially rolled configuration, thus inhibiting the formation of sharp fold edges. The terms "small opening" or "small incision" means an opening that is less than about 5 mm wide and/or long, typically about 3 mm. The term "compact configuration" means that the donor disc is configured smaller than its end use configuration by at least about 40%, typically less than about 50%. For example, if the end use configuration is about an 8.25 mm diameter or width, then the compact configuration can provide a width that about or less than about 5 mm, typically about or less than 4 mm. In some configurations, the compact configuration can be about 60% less than the use or normal width, such as about 3 mm or less, and may be about 2.5 mm.

Turning now to the figures, FIG. 1A illustrates a medical tool 10 and a donor tissue graft implant 25. The donor implant is typically a disc such as a posterior lamellar keratoplasty transplant (PLK), although other tissue grafts, particularly fragile tissue grafts, may be suitable for forming and/or delivery using devices/methods described herein. As shown in FIG. 1A, in some embodiments, the tool 10 can cooperate with a flexible substrate carrier 15 that holds the implant 25. The holding portion 15e of the flexible substrate 15 can be configured to have a substantially planar shape outside the tool 10.

Figure 1B:
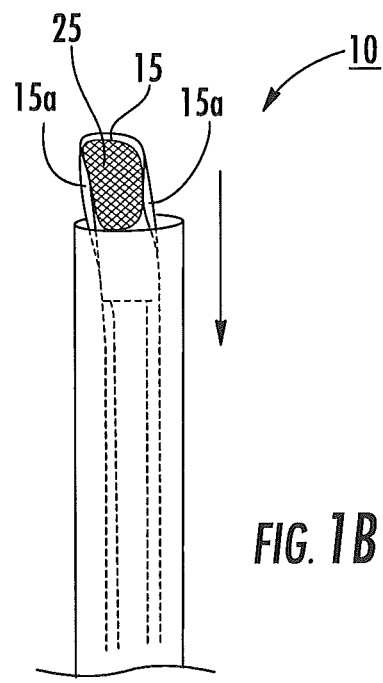
FIG. 1B is a schematic illustration of the device shown in FIG. 1A showing the flexible substrate and tissue graft being retracted into a holding chamber according to embodiments of the present invention.
Figure 2:
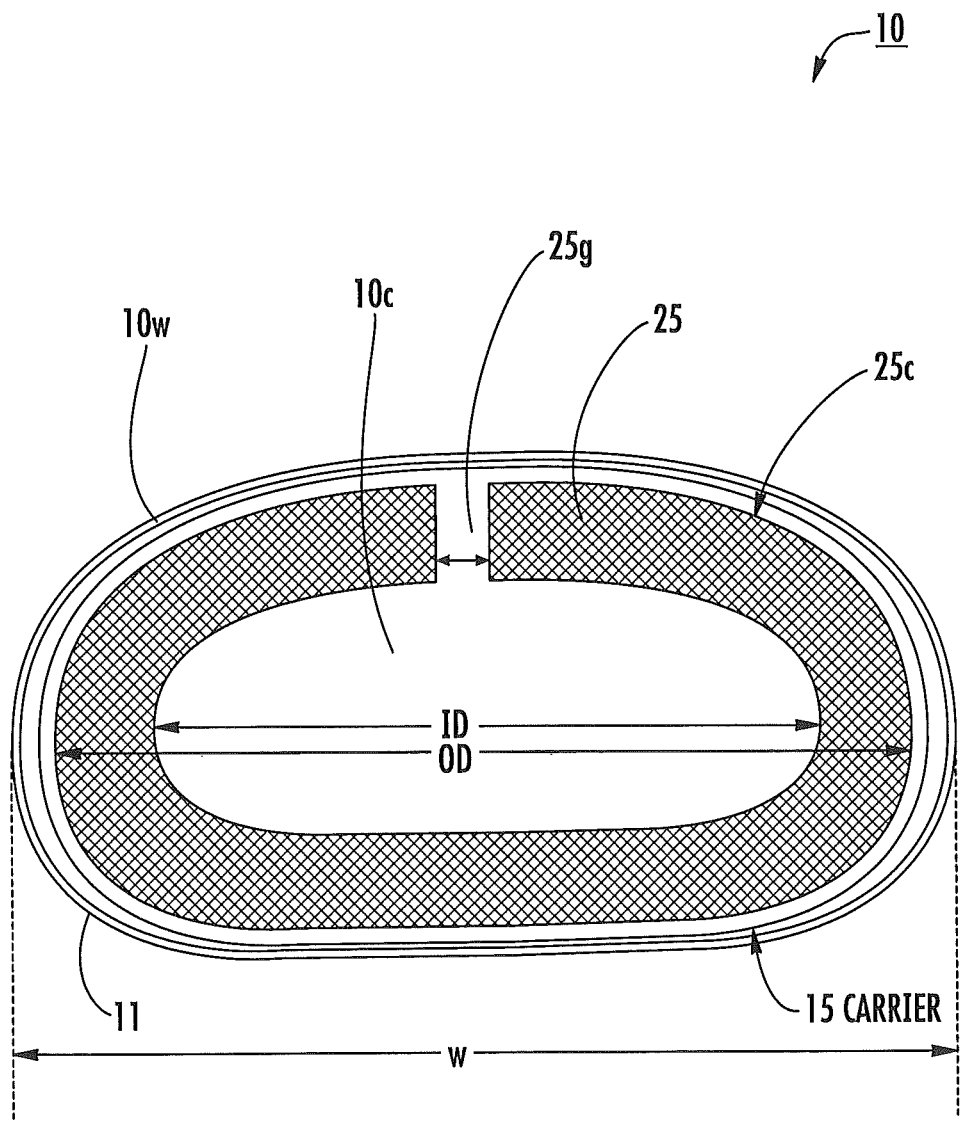
FIG. 2 is a greatly enlarged cross-sectional view of the device shown in FIGS. 1A and 1B with a fully retracted flexible substrate with tissue graft according to some embodiments of the present invention.

As shown in FIGS. 1B and 2, the tool 10 has a cavity 10c that is configured to slidably receive a flexible substrate carrier 15 that holds the donor disc 25. As shown in FIG. 1B, as the flexible substrate 15 enters (is retracted, withdrawn and/or pulled into) the tool cavity 10c, the outer edges of the flexible substrate 15a, 15b are pushed upward and can also be forced to travel closer together, thereby forming the donor implant 25 into a smaller, typically compact, configuration using the flexible substrate 15. The flexible substrate can be comfortable so as to substantially conform to the shape of the cavity wall 10w. As the flexible substrate 15 takes on a compact configuration, it forces the tissue graft 25 into a smaller, compact configuration.

As shown in FIG. 2, the flexible substrate 15 can be pushed, folded, wrapped or bent, and is typically formed to have a curvilinear cross-sectional shape 25c with the two opposing edge portions spaced apart to define an open center space 25g. However, the flexible substrate 15 and donor tissue graft 25 can be formed into other shapes. The compact tissue graft shape can be a rolled shape without sharp fold creases, corners or edges. As shown, the curvilinear shape 25c can be substantially oval with rounded lateral edges. The cavity 10c can have a width W that is between about 3-6 mm, typically between about 3.5 mm to about 4 mm. The outside diameter (OD) of the disc in the shaped configuration 25c can be between about 2.5 mm to about 3 mm, typically about 2.87 mm for a 9 mm graft. The inside diameter (ID) of the shaped disc 25c can be between about 0.1 mm to about 0.5 mm less than the OD, depending on thickness of the graft 25. For the 2.87 mm OD and a tissue graft having a thickness of about 150 μm, the ID can be about 2.84 mm.

Figure 3:
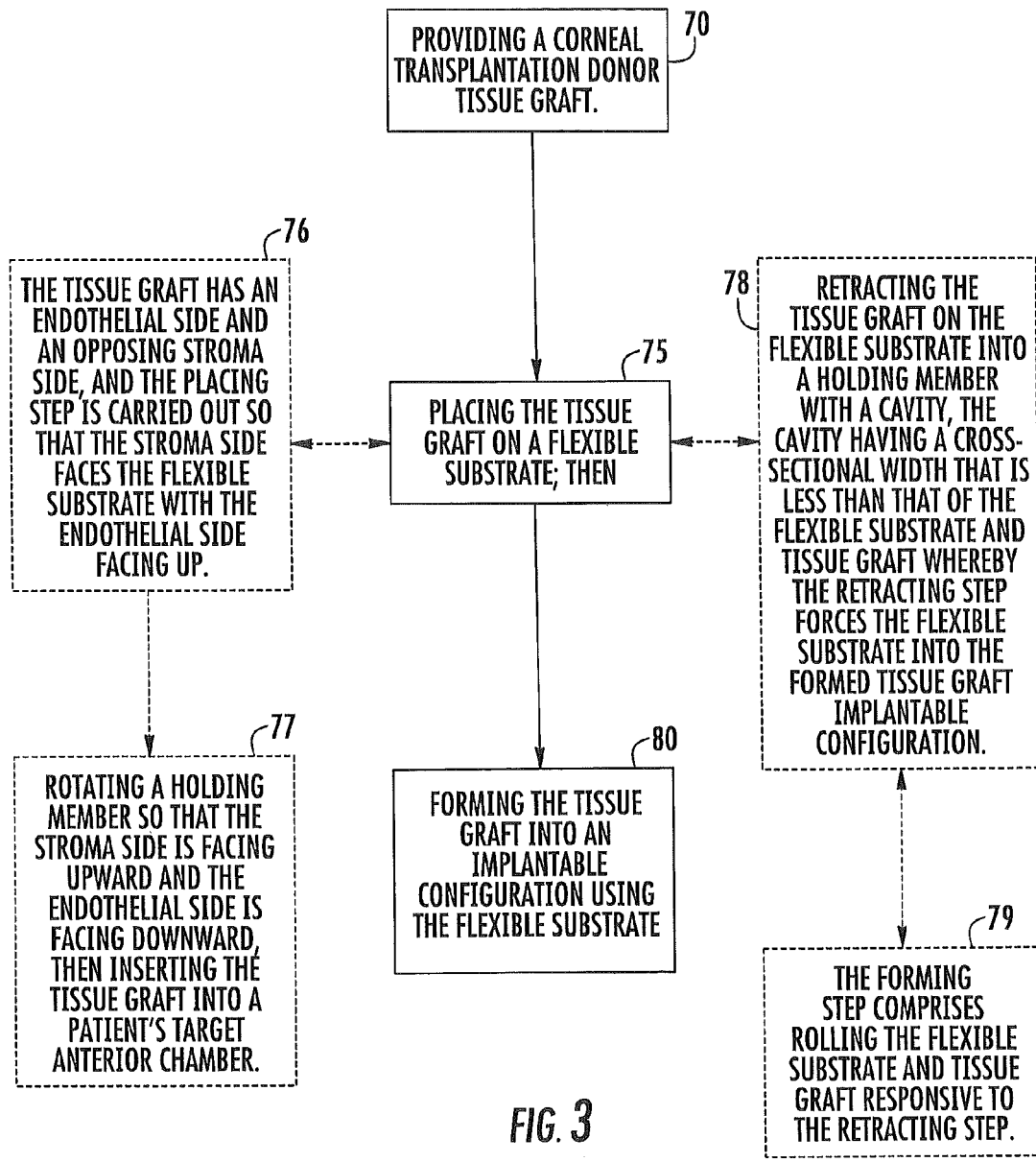
FIG. 3 is a flow chart of operational steps that may be taken to carry out embodiments of the present invention.
Figure 33:
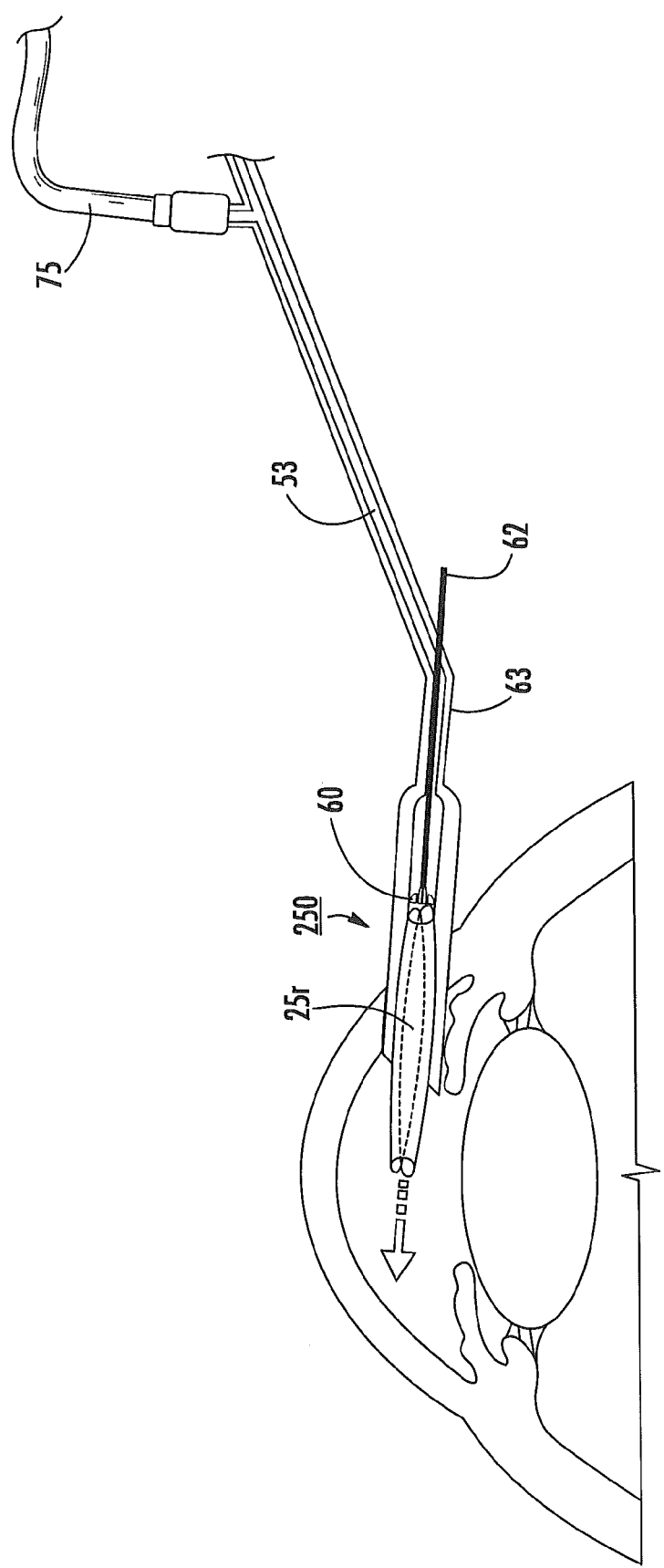
FIG. 33 is a schematic illustration of the device and rolled donor disc being delivered to a recipient stromal bed to carry out a small incision DLEK according to embodiments of the present invention.

FIG. 3 illustrates operational steps that can be used to configure a deep stromal endothelial donor corneal disc for transplantation. A corneal transplantation donor tissue graft can be provided (block 70). The tissue graft can optionally be placed on a flexible substrate (block 75), then the tissue graft can be formed into an implantable configuration using the flexible substrate (block 80). The forming can be carried out substantially (if not totally) without endothelial cell trauma. FIG. 33 illustrates an exemplary target implantation site.

In some embodiments, the tissue graft has an endothelial side and an opposing stromal side, and the placing step is carried out so that the stroma side faces the flexible substrate with the endothelial side facing up (block 76). The holding member can be rotated so that the stromal side is facing upward and the endothelial side is facing downward before inserting the tissue graft into a patient's target anterior chamber (block 77).

In some embodiments, the tissue graft can be retracted on the flexible substrate into a holding member with a cavity, the cavity having a cross-sectional width that is less than that of the flexible substrate and tissue graft, whereby the retracting step forces the flexible substrate into the formed tissue graft implantable configuration (block 78). In other embodiments, a supplemental tool can help form the substrate and disc into a compact configuration, independent of, outside of and/or in cooperation with the holding member. The forming can include rolling the flexible substrate and tissue graft responsive to the retracting step (block 79).

The flexible substrate 15 can be formed from a unitary layer of biocompatible material or laminated layers of biocompatible materials. The flexible substrate 15 can comprise any suitable biocompatible material, such as elastomer, polymer, and copolymer materials and/or derivatives thereof, mylar, foil and the like, and/or combinations thereof. Biocompatible non-stick and/or antifriction coatings may be used. The flexible substrate 15 can include a first anti-friction coating on one primary surface and a different coating on the tissue-contacting surface. The flexible substrate 15 can be a thin-film substrate.

As shown in FIG. 2, the flexible substrate 15 can be thinner than the tissue graft 25. In some embodiments, the flexible substrate 15 is less than half the thickness of the graft 25. In particular embodiments, the flexible substrate 15 can be between about 1-200 μm thick, and more typically between about 10-100 μm thick.

Figure 4A:
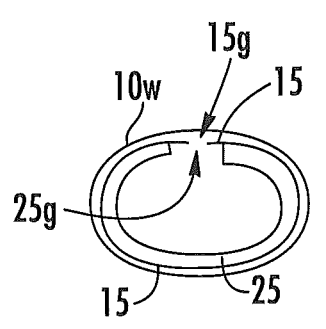
FIGS. 4A-4C are exemplary cross-sectional views taken along lines 4-4 in FIG. 5.
Figure 4B:
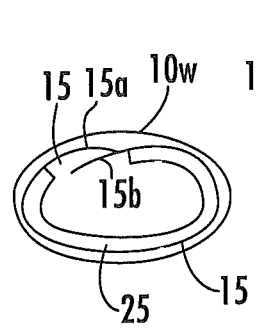
Figure 4C:
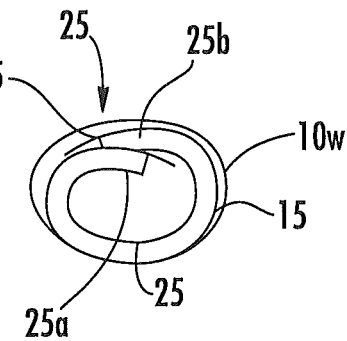

As shown in FIGS. 4A-4C, the curvilinear formed tissue graft shapes 25c and flexible substrate 15 can be configured so that respective opposing edges are spaced apart with gaps 25g, 15g axially extending about a medial portion of the holding member cavity 10c as shown in FIG. 4A. Alternatively, the substrate edges 15a, 15b may contact and even overlap as shown in FIG. 4B. Optionally, as shown in FIG. 4C, the disc 25 may be rolled so that one edge 25a is under the other edge 25b. It is noted that the cross-sectional shape of the holding cavity 10c is shown in FIGS. 2 and 4A-4C as being substantially oval or circular; however, the instant invention is not limited thereto. Other geometric shapes may also be employed, such as, for example, pentagonal, hexagonal, square, rectangle, triangular, and the like.

Figure 5:
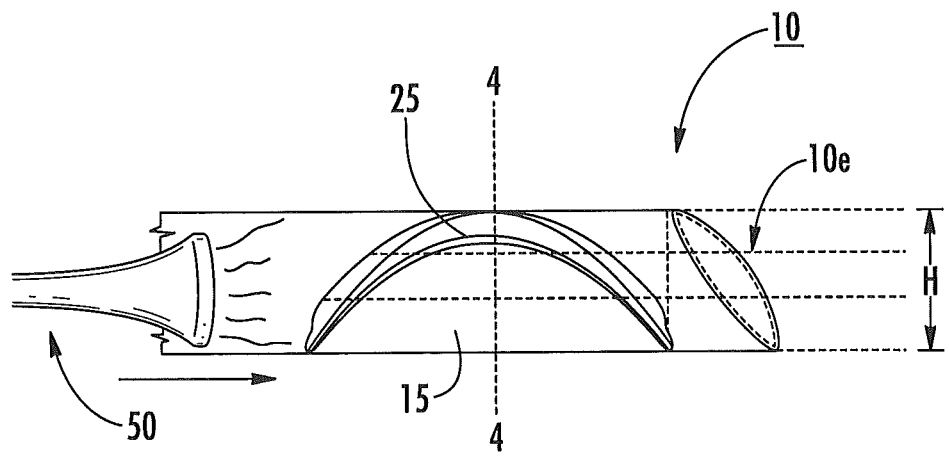
FIG. 5 is a partial side view of the device shown in FIGS. 1A and 1B.

FIG. 5 is a side view of the holding device 10 with the formed disc 25 on the flexible substrate 15. As shown, the device 10 includes an angled or tapered forward edge portion 10e to facilitate insertion into the anterior chamber during implantation and/or delivery. The height H of the cavity 10c can be between about 3-6 mm, typically between about 3.5 mm to about 4 mm. FIG. 5 also illustrates that a plunger 50 can be disposed upstream of the formed disc 25. Fluid from the plunger 50 and/or the plunger itself can be used to expel the tissue graft 25 from the cavity during surgical placement. Other irrigation delivery configurations may also be used. In some embodiments, the flexible substrate 15 is retained in the holding device 10 during delivery of the tissue graft 25. In other embodiments, the flexible substrate 15 can be advanced with the disc during transplant placement in the eye.

Figure 6:
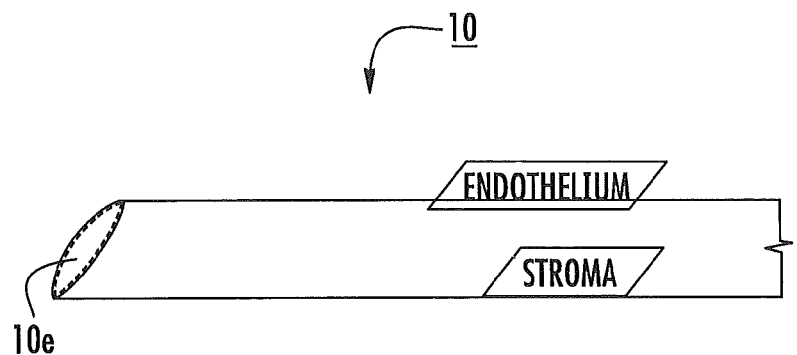
FIG. 6 is a schematic side view of the device shown in FIG. 5 illustrating an implant orientation of the tissue graft in the device according to some embodiments of the present invention.

FIG. 6 illustrates that the device 10 can have a harvest configuration and a delivery configuration with different orientations for holding and releasing, respectively, the transplant tissue 25. As shown, it is typically desirable to have the endothelium side of the tissue facing upward and the stromal side oriented (facing) down during harvest or preparation, and to reverse the orientation for ease of placement upon release of the implant from the cavity 10c. As the implant leaves the cavity 10c (after the device is inserted into a small incision proximate the target anterior chamber bed), the disc 25 is no longer constrained by the wall of the device 10 and can automatically unfold or unroll to a substantially planar configuration with the stroma side facing up.

Figures 7A, 7B, 7C:
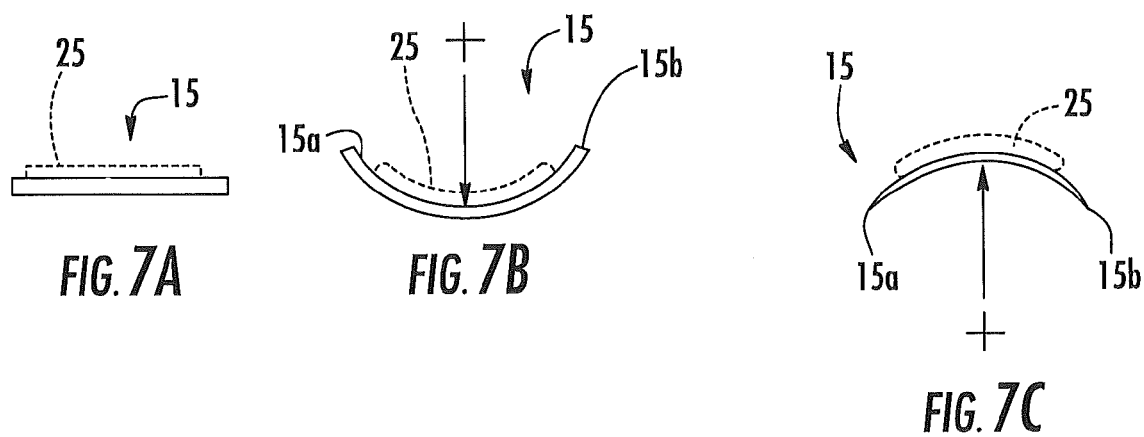
FIGS. 7A-7C are side views of flexible substrates for receiving donor tissue during a harvesting procedure according to some embodiments of the present invention.

FIGS. 7A-7C illustrate exemplary configurations of the flexible substrate 15 when obtaining the donor tissue grant from a harvesting procedure. The donor tissue graft 25 can be placed on the substrate 15 when the carrier substrate is in the substantially planar configuration (FIG. 7A). In other embodiments, the carrier substrate 15 may be configured to have a concave or convex curvature as shown, for example, in FIGS. 7B and 7C, respectively. The donor graft 25 can be placed on an upper surface of the substrate 15, then formed into a more compact configuration. If concave or convex configurations are used, the forming may follow the direction of the curvature. For example, the outer edges 15a, 15b can be pushed upward for the configuration shown in FIG. 7B and the outer edges 15a, 15b can be pushed downward in the embodiment shown in FIG. 7C.

FIG. 8A illustrates that the flexible substrate 15 can be attached to an arm 16. The arm 16 can be rigid or have increased rigidity with respect to the flexible substrate 15. The arm 16 can be releasably attached to the substrate 15 or fixedly attached to the substrate 15. FIG. 8B illustrates that the flexible substrate 15 can include an integral, rearwardly extending arm 15r that extends away from the forward holding portion of the substrate 15e. The arm 15r may be attached to a stiffener member or may be laminated or otherwise structurally reinforced for increased rigidity. The arm 15r, 16 can engage the flexible substrate 15 and be used to pull the substrate into the cavity of the tool 10.

Typically, the donor disc 25 is placed on a first (upper) surface of the flexible substrate 15 with the stroma side contacting the substrate 15. The substrate 15 is then retracted into the holding cavity 10c. The device 10 is rotated, typically about 180 degrees, to place the stroma side up, with the endothelium side facing down. The end of the device 10e can be inserted into the eye's anterior chamber and the tissue ejected, expelled or otherwise released.

FIGS. 9A-9C illustrate exemplary flexible substrate end portion (paddle) configurations 15e. As shown in FIG. 9A, the flexible substrate 15 can have an elongate body with a rounded arcuate forward edge portion 15e that merges into two parallel side portions. As shown in FIG. 9B, the flexible substrate forward edge portion 15e can be substantially circular, and as shown in FIG. 9C, the forward edge portion 15e can be rectangular. The flexible substrates 15 can include visual alignment indicia 18 for facilitating proper placement during the harvesting procedure.

In some embodiments, the holding device 10 can be configured to inhibit rotation of the flexible substrate 15 inside the cavity 10c to positively control and maintain the orientation of the flexible substrate 15 as the tissue 25 is retracted and/or advanced. In this arrangement, the stromal and endothelial sides are known and controlled, oriented to a user's control, and/or positioned so that the orientation for placement can be easily determined or known.

Figure 10A:
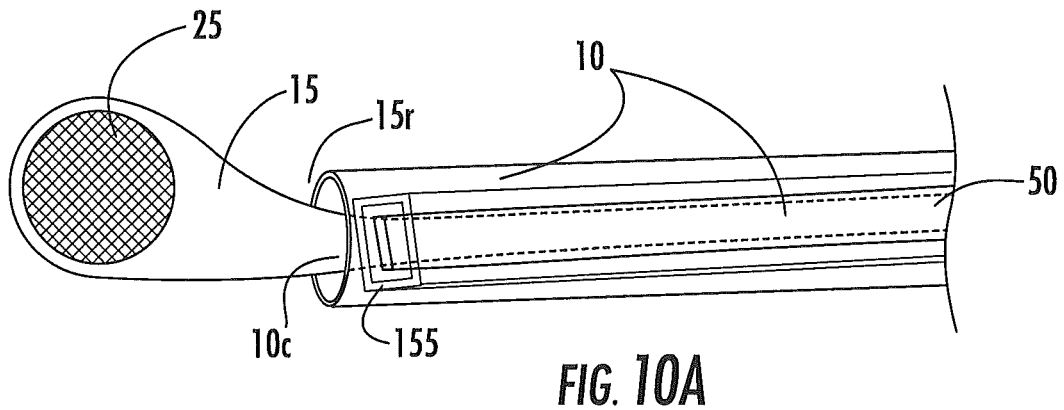
FIG. 10A is a schematic top view of a flexible substrate with a collar according to some embodiments of the present invention.
Figure 10B:
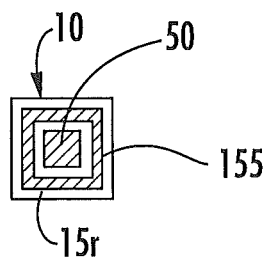
FIG. 10B is a lateral section view of an anti-rotation configuration of the collar shown in FIG. 10A according to some embodiments of the present invention.

FIG. 10A illustrates that the flexible substrate 15 can be configured to slidably retract into the tool body 10. The substrate 15 can be attached to a collar 155 that can be angled and configured to slide in a single controlled orientation within the cavity 10c during advancement and retraction. In some embodiments, the substrate 15 can communicate with the collar 155 to inhibit rotation inside the cavity 10c and to allow the substrate 15 to translate axially only in the retraction direction. As shown in FIG. 10B, the collar 155 can receive the plunger 50 and allow the plunger 50 to advance without advancing the flexible substrate 15. In other embodiments, the substrate 15 can advance with the plunger 50 and/or fluid to help position the disc 25 in a target location. The cross-sectional shape of the plunger 50 can also be angled to be matably received by the collar 155 to maintain the orientation of the plunger 50 with respect to the flexible substrate 15 and/or cavity 10c. The plunger 50 may include fluid apertures (not shown) and/or fluid may enter in advance of the plunger 50 and/or via the gap spaces between the plunger 50 and collar 155. The plunger 50 and/or fluid can be introduced over or under the arm 15r to force the donor disc 25 from the cavity 10c with the flexible substrate 15 remaining in the cavity 10c.

Figure 10C:
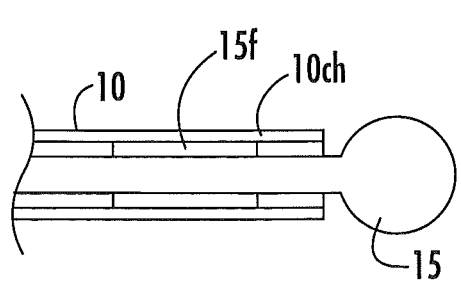
FIG. 10C is a partial longitudinal section view of an anti-rotation configuration to inhibit rotation of the substrate in the chamber according to embodiments of the present invention.
Figure 10D:
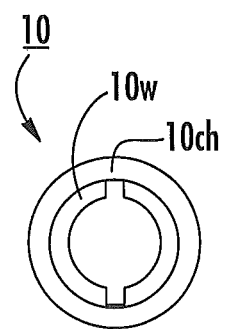
FIG. 10D is a lateral cross-sectional view of the device shown in FIG. 10C illustrating a fin channel.

FIG. 10C illustrates an alternate exemplary anti-rotation configuration of the flexible substrate 15. As shown, the flexible substrate 15 can include at least one fin 15f (shown as two) that can slide in a mating channel/recess 10ch (FIG. 10D) in the wall 10w of the tool 10. The channel or recess 10ch may alternatively reside in the substrate collar 155 or other component rather than in the wall of the device.

Figure 11A:
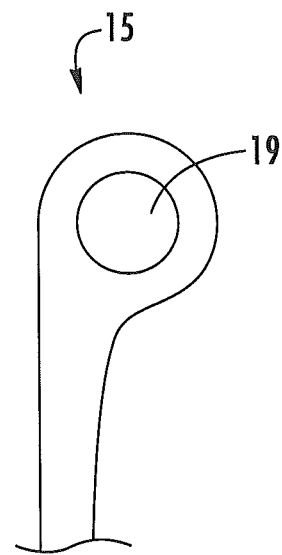
FIG. 11A is a schematic partial top view of another flexible substrate configuration according to embodiments of the present invention.
Figure 11B:
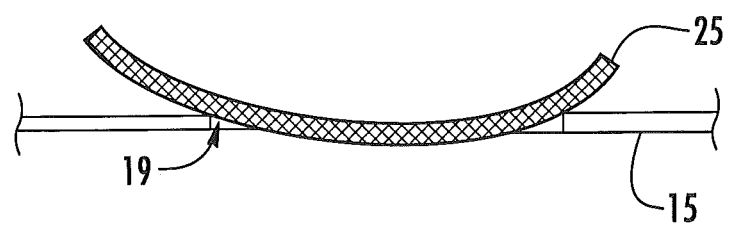
FIG. 11B is a greatly enlarged partial side view of a tissue graft on the flexible substrate shown in FIG. 11A according to some embodiments of the present invention.

FIG. 11A illustrates that the flexible carrier substrate 15 can include a well 19. The well 19 can be a depression formed in the substrate 15 or an aperture. The well 19 can reduce surface tension to facilitate the ability of the flexible substrate 15 to roll or wrap to a compact configuration. FIG. 11B illustrates the donor tissue graft 25 placed over the well 19 prior to rolling or forming.

As noted above, the plunger 50 can be configured to advance based on pressurized fluid and/or rod actuation. If pressurized fluid alone is used, no separate plunger arm or plunger arm channel is required (not shown). In any event, where a plunger 50 is employed, the plunger 50 may be configured directly (gently) contact a trailing edge of the rolled disc 25c, or may be configured to push indirectly, such as by pushing an intermediate fluid such as a gel (comprising, for example, a viscoelastic material) forward, thereby pushing the disc forward.

Alternatively, fluid can be introduced into the chamber 10c and directed to flowably expel the disc 25c (FIG. 2) into position in the anterior chamber. The plunger 50 can be advanced to help expel the disc 25c as needed. The delivery device 10 can include a plurality of spaced apart flow orifices (and may include micronozzles) that are configured to introduce fluid from a wall and/or from the plunger of the device into the chamber 10c. The orifices have an associated fluid channel that can merge into the primary channel. The orifices can reside axially and circumferentially spaced apart about the chamber 10c or may reside substantially aligned in a rearward portion of the chamber 10c to help initiate the expellant flow force onto the disc 25c. The orifices may be configured as flushing ports that can expel pressurized fluid generally inward and axially forward. Alternatively, the orifices can be configured to emit fluid under lesser pressures to inhibit adhesion to the chamber walls.

Figure 12:
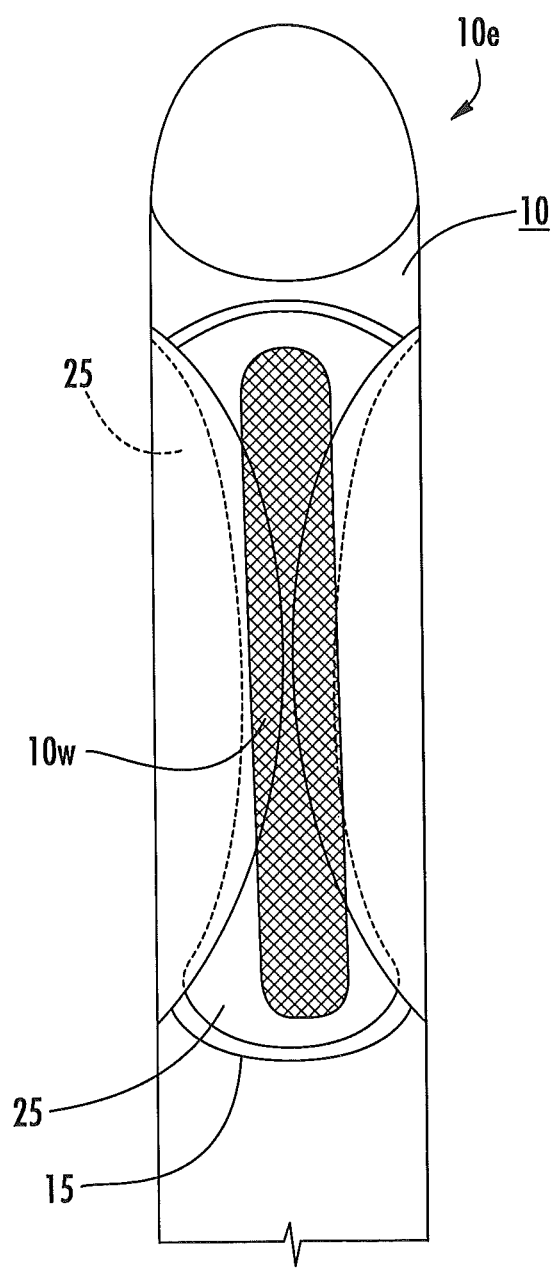
FIG. 12 is a schematic partial top view of a holding device configured to allow a user to view internal objects to visually confirm a desired orientation of the transplant tissue graft according to embodiments of the present invention.

FIG. 12 illustrates that the holding member 10 can be configured to allow a user to view internal components to observe orientation of the graft and/or withdrawing, retracting, rolling and/or advancing action to visually confirm orientation of the graft 25. The holding member 10 itself can be visually transmissive, such as transparent or translucent, or may include at least one viewing window. If the latter, there are typically at least two viewing windows, spaced apart so that one resides above the other. As shown, a first viewing window 10w (illustrated by the cross-hatch markings) can axially extend over at least a major portion of the length of the tissue graft 25, typically a substantial length and with a width sufficient to allow a clinician to verify that the endothelial side is in position for implantation.

The tool 10 can be a multi-purpose, bidirectional tool that receives donor tissue, forms the donor tissue, holds the donor tissue, then is used to surgically deliver (expel) the donor implant 25.

It is contemplated that rolling the donor disc 25 can reduce damage to the donor endothelium over folded configurations and/or provide for smaller entry configurations. The donor disc 25 can have a typical use diameter that is between about 8.0 mm to about 9.0 mm, typically between about 8.0 mm to about 8.25 mm; however, other suitable diameters may be used. The disc 25 may also have a thickness that is typically between about 100-300 μm thick, and more typically between about 100-200 μm thick.

Figure 13:
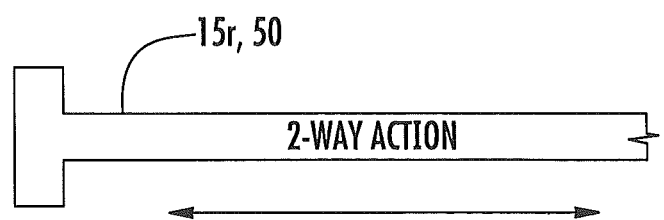
FIG. 13 is a schematic partial side view of a 2-way action medical tool according to some embodiments of the present invention.
Figure 14:
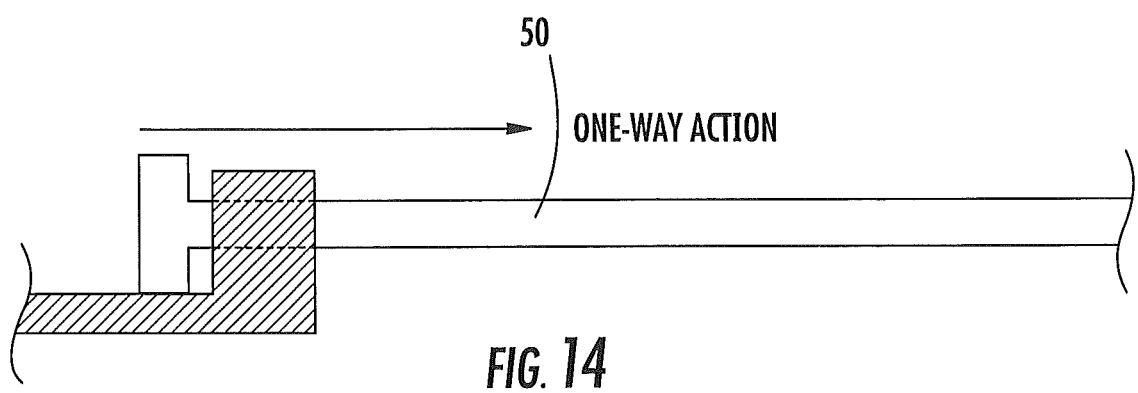
FIG. 14 is a schematic partial side view of a one-way action medical tool according to other embodiments of the present invention.

FIG. 13 illustrates that the plunger 50 and/or flexible substrate 15 can be configured to operate with two-way action, while FIG. 14 illustrates that the plunger 50 (and/or flexible substrate 15) can operate with one-way action. For the latter, the plunger 50 can translate to extend, whereas the flexible substrate 15 can translate to retract. Each may have a collar or other stop member that defines the stroke and/or directional travel.

Figure 15:
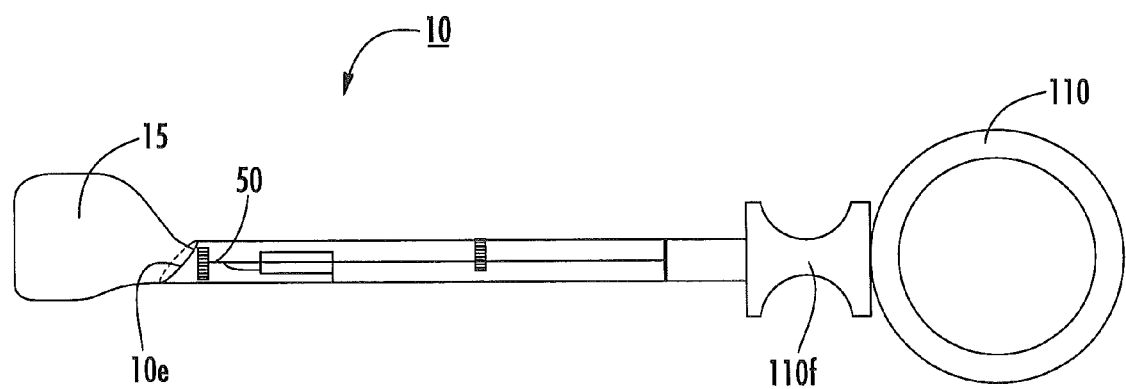
FIG. 15 is a schematic side view of a medical tool with a cooperating flexible substrate according to embodiments of the present invention.

FIG. 15 illustrates a thumb handle control actuator 110 with a finger post 110f that can be used to operate the tool 10 during a surgical procedure. Turning the thumb handle control actuator 110 can retract the flexible substrate 15 into the tool cavity 10c and/or push the plunger 50 forward to expel the tissue graft 25 during surgical implantation.

The donor disc 25 can be extracted from the donor eye in any suitable manner. Similarly, the desired size disc of the posterior corneal stroma of the recipient eye can be resected in any suitable manner, such as by using instrastomal scissors (such as "Cindy Scissors" from Bausch & Lomb).

Typically, the tool 10 forms the disc 25 so that the lower donor stromal surface is on the outside bottom surface of the rolled body 25c (FIG. 2).

To promote reliability, efficiency and/or ease in surgical placement, it is contemplated that a standard rolled orientation will be used and/or that different medical kits noting the surgeon's desired rolled orientation can be provided. The latter can allow a surgeon to order a kit that is suitable for the particular entry incision used (which may vary depending on patient eye structure) and/or for a desired unrolling technique (side to side, top to bottom, bottom to top, offset, and the like). The rolled disc 25r may be configured for a temporal side or a superior entry. When unrolling in situ, rather than placing the rolled disc medially in the recipient stromal bed, the rolled disc 25r (FIG. 5) may be inserted closer to a side edge portion of the eye, the side edge portion typically being the one that corresponds to the last rolled portion. The donor disc can then be unrolled in an opposite direction using physical or fluid forces.

To promote increased efficiency in surgical procedures, an OEM or medical company can provide the donor disc 25 preformed in the rolled configuration 25r (FIG. 5) and ready for surgery. The rolled disc 25c may be held in a refrigerated storage condition prior to end use. The disc 25 may be rolled using different end use disc sizes and provided in a preformed rolled configuration for different end use sizes (between about 8 mm to about 9 mm, including about 8.25 mm).

The chamber 10c has a length L sufficient to hold the length of the disc 25 therein, and is typically between about 8.5-10 mm long, typically about 9 mm long. As noted above, pressurized fluid can be introduced into the chamber 10c to urge or force the rolled disc 25c to exit the chamber. The fluid can comprise air, oxygen, saline, water or other suitable fluid. Where a lubricant and/or viscoelastic substance (such as HEALON from Pharmacia in Nutley, N.J.) is used to preserve or protect the rolled disc 25r, a pre-delivery flushing may be desired to prepare the rolled disc 25r for surgical insertion (to remove at least some of the substance from the rolled disc 25r or chamber 10c prior to placement in the body). The open-end 10e may be capped or sealed prior to use to help seal the disc in a sterile environment and/or placed in a sterile sealed package.

FIG. 16 illustrates an example of a medical tool kit 200 that can be provided to obtain donor tissue 25. The kit 200 includes a forming tool (holding member) 10 and a flexible substrate 15 in a sterile package 90. The kit 200 may also include fluid 21 that can be placed on the donor tissue 25 before or after insertion into a holding member 10. The fluid 21 can comprise a quantity of biocompatible liquid that can be placed about the disc 25 in a sealable package. The liquid 21 can comprise sterile water, saline, viscoelastic material and the like.

FIG. 17 illustrates a medical kit 300 that includes a preformed (wrapped, folded and/or rolled) donor disc 25c that may be releasably held in the holding member 10. The medical product 300 can be held in a sterile package 90. The package 90 can be a flexible package, such as an elastomeric- or foil-backed elastomeric package, or a rigid substrate package. Combinations of flexible and rigid packaging materials can also be used.

A fluid channel (conduit or other fluid channel configuration) can be provided as a separate tool in the kit 300 or may be provided as one of a standard component in a surgical suite. The fluid channel can be configured to engage a pressurized fluid flow source (such as a syringe, a cylinder, or other flow source) at a surgical site.

The kit 200, 300 and/or tool 10 can be labeled as single-use disposable. The tool 10 (at least the forward body thereof) can comprise a sufficiently strong and relatively rigid elastomer, composite or ceramic or may comprise a metal, such as stainless steel. Combinations of these types of materials may also be used. In other embodiments, the tool 10 can be resiliently configured with sufficient structural rigidity to hold and form the disc 25c.

FIGS. 18A and 18B illustrate that the combination harvesting tool and delivery device 10 may be configured with visual alignment indicia 31i, 31o. The alignment indicia 31i, 31o can comprise arrows, text, color or marked regions on an external viewable surface of the respective devices. For example, arrows or other indicia 31i, 31o on a forward portion of the holder body can help an operator retract (arrow in, 31i) and implant (arrow out, 31o) a disc 25r in a desired orientation into the anterior chamber. This can facilitate reliable and proper positioning for enhanced operative positioning of the disc in the stromal bed. In other embodiments, no indicia is needed on the delivery device 10 as the configuration can be, visibly unique (i.e., the holding member body may be configured so that the implantation orientation is visually different from a side or bottom portion) and the operator can align the indicia 31 with the target orientation of the delivery device, based on the configuration of the body.

FIGS. 19A and 19B illustrate another embodiment of a tool 10' that can cooperate with a flexible substrate 15 to form a donor disc 25 into a compact shape for implantation according to other embodiments of the present invention. As shown, two spaced apart prongs 12, 14 can hold the flexible substrate and tissue graft 25 and roll the tissue and substrate into a desired configuration. A collar 30 can be advanced to lock the tool holding the rolled or formed tissue 25 and flexible substrate 15.

Figure 20A:
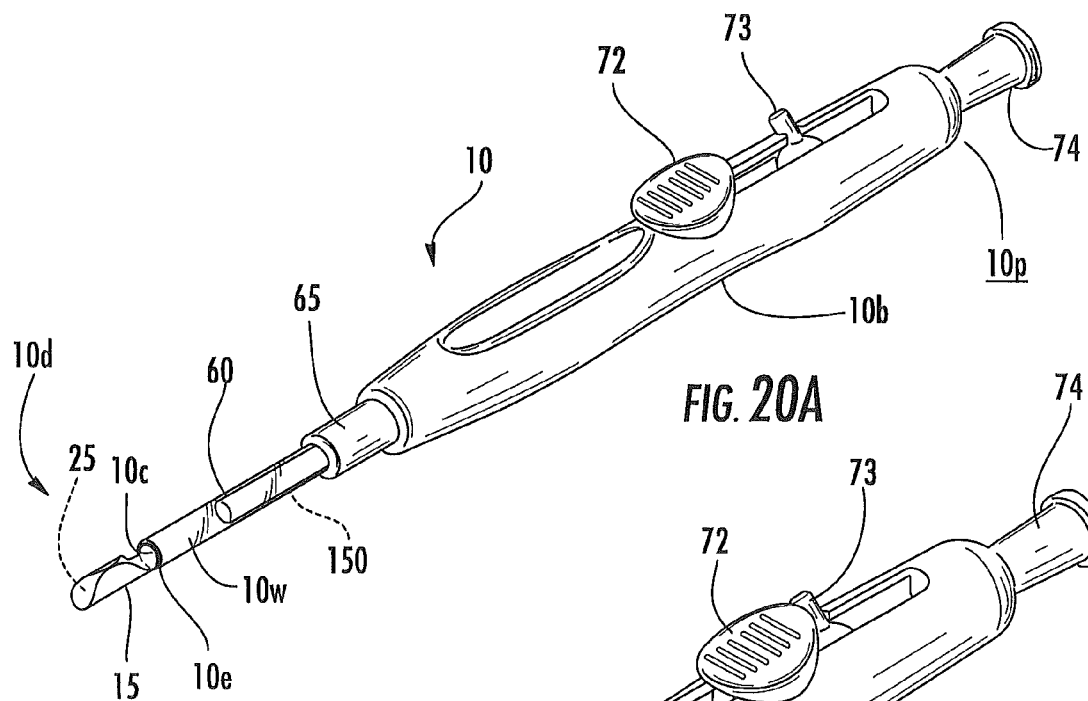
FIGS. 20A-20C are schematic perspective views of a medical tool that can be used to hold and/or deliver donor disc tissue according to embodiments of the present invention.
Figure 20B:
Figure 20C:
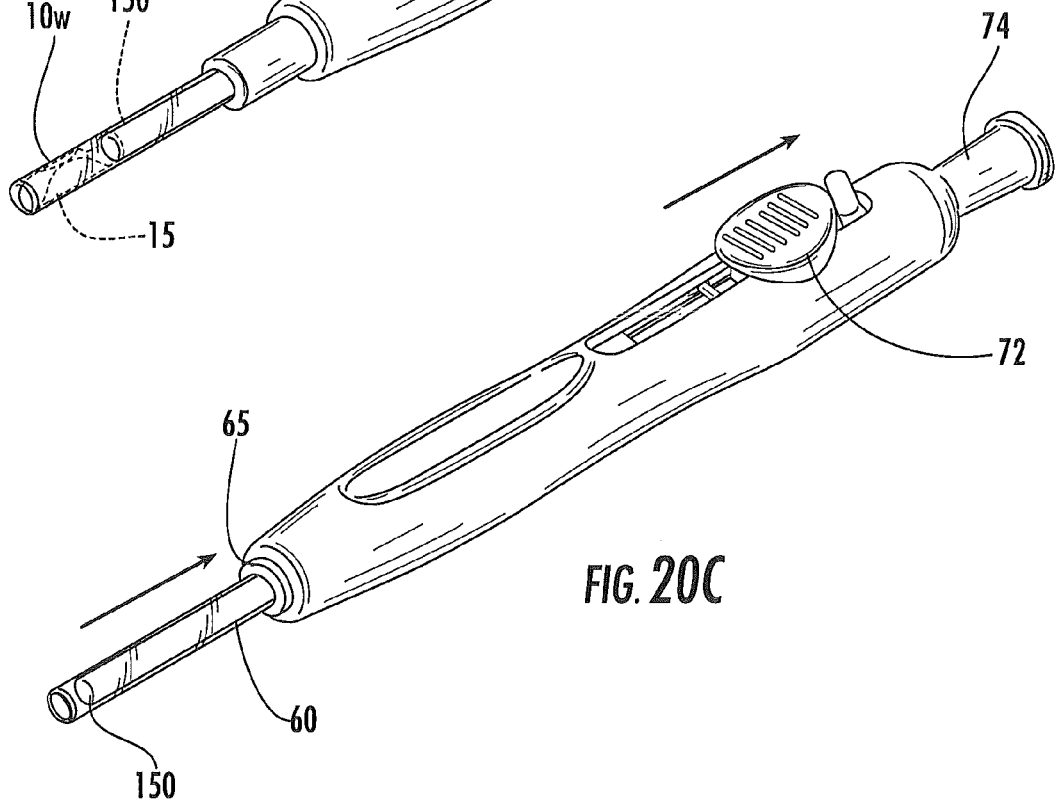

FIGS. 20A-20C illustrate another embodiment of a tool 10 that can hold and/or deliver the tissue 25 to a patient. As shown in FIG. 20A, the device 10 includes a carrier substrate 15 that is configured to hold the tissue graft 25. The carrier substrate 15 can be a biocompatible, pre-shaped carrier. The tissue graft 25 can be drawn into the cannula 60, which can be described as a delivery barrel. The forward end portion of the cannula 60 can include a tapered end 10e and can have a size (cross-sectional area and/or diameter) may allow for a self-sealing entrance wound, if desired.

As is also shown, the tool 10 includes a first cannula 60 (which can define at least a portion of a holding chamber) that is configured to slidably receive and hold the carrier substrate 15, and a second cannula 65 that is attached to the first cannula 60 and that can be configured to slidably retract into the tool body 10b. The tool 10 may also include a user slide control member 72 in communication with the carrier substrate 15 and, optionally, the cannula 65.

As shown in FIG. 20B, the substrate 15 with the target implantation tissue 25 can be slidably retracted into the cannula 60 and held for subsequent delivery to a patient in this configuration. A sterile covering 90 (FIG. 22), such as a biocompatible, sterile pouch or bag, may be used to encase the loaded tool 10. The device 10 can be retained in the retracted "hold" configuration and packaged in a sterile kit for longer term storage and shipment, or the device 10 can be loaded and used at a single clinical site, even as preparation for and/or during a patient surgery.

FIG. 20C illustrates that, during actual implantation, once at a target implantation site, the second cannula 65 can be retracted substantially in concert with the substrate 15 to expose the tissue 25. As the first cannula 60 is attached to the second cannula 65, the first cannula 60 is also retracted, leaving the tissue 25 forward of the tissue delivery member 150 and out of the device 10. This way a surgeon can orient the implant tissue 25 (e.g., donor cornea) while held in the tool 10 inside the eye in the cannula 60, and when the cannula 65 is retracted the tissue 25 remains substantially in the desired position at the target implantation site.

The slide control member 72 can be configured to translate from an empty (ready to load) position (FIG. 20A), to a retracted "hold" position (FIG. 20B), then to a second retracted "delivery" position (FIG. 20C). The slide control member 72 can be moved from the first to the second position to slide the tissue 25 on the substrate 15 into the first cannula 60 while the first and second cannulas 60, 65 and tissue delivery member 150 remain substantially stationary. During a surgical procedure, the slide control member 72 can be axially slid further away from the patient, thereby retracting the first and second cannulas 60, 65 and the substrate 15 and exposing the tissue 25. To inhibit inadvertent and/or premature release and/or exposure of the implant tissue 25 from the tool 10, the slide control member 72 can cooperate with a locking member 73. The locking member 73 can be configured to inhibit further retraction of the substrate 15 as well as retraction of the cannulas 60, 65 and/or substrate 15 until actual delivery is desired.

Figure 21:
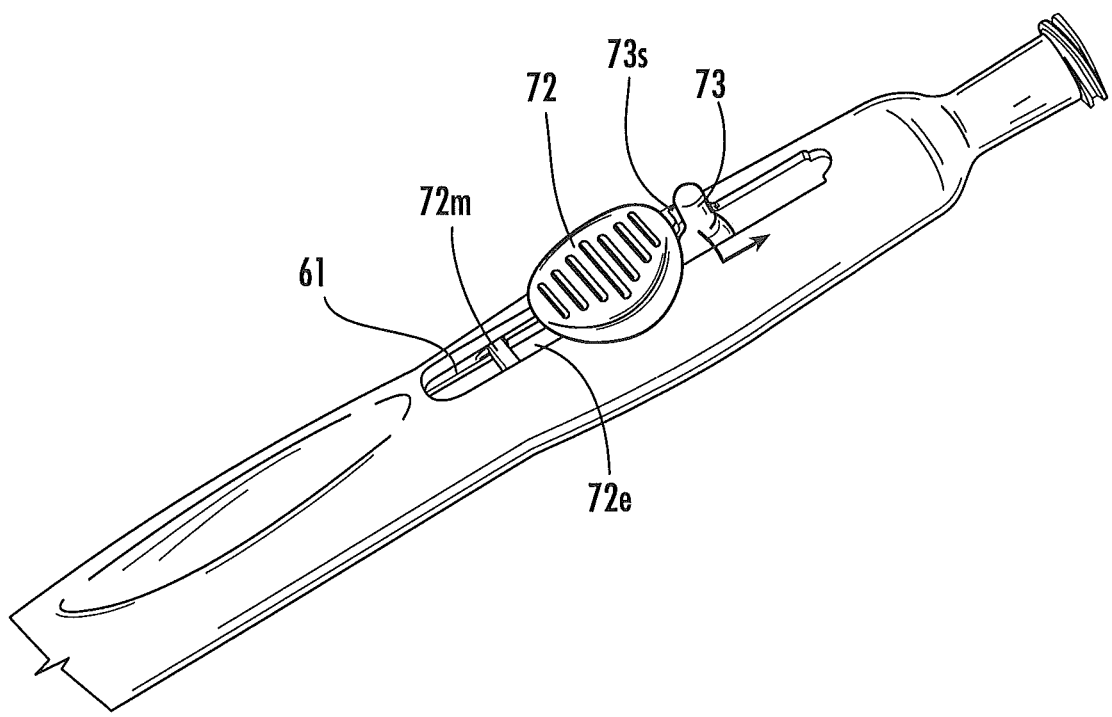
FIG. 21 is a schematic of an enlarged partial perspective view of the device shown in FIGS. 20A-20C.

As shown in FIG. 21, the slide control member 72 can comprise a "thumb" or finger interface (e.g., a slide button or key) which is attached to the substrate 15 with a slide extension 72e. The tool body 10b can be configured with a slot 73s that slidably receives and matably holds the lock member 73 in position. The lock member 73 can be attached to the cannula 65 with an axially extending slide extension 61. To disengage the lock member 73, a user can laterally move the lock member 73 out of the slot 73s. The slide extension 72e can be biased to axially translate to allow a mating segment 72m (such as a tab or protrusion) of the slide extension 72e to engage the slide extension 61 (such as via a mating slot or key form). The locking engagement of the slide extensions 72e, 61 can maintain a desired alignment of the cannula(s) with the substrate and donor tissue 25. In operation, after the lock member 73 is disengaged, as the slide control member 72 retracts, the substrate 15 and the cannulas 60, 65, retract substantially in concert therewith.

In other embodiments, two separate slide controls may be used to retract the cannulas 60, 65 and substrate 15 separately, either independently or dependently (not shown). Similarly, the lock member 73 can be configured in other ways to inhibit premature sliding, such as, but not limited to, having a removable external locking ring that engages a stationary tab (not shown).

It is also noted that, instead of two cannulas 60, 65 as shown, for example, in the embodiment in FIGS. 20A-20C, a single sliding cannula may be used (not shown). If so, the single cannula may be stepped in diameter size (typically more narrow toward the penetration tip end). In any event, in some embodiments, at least the forward portion of the first cannula 60 can be visually transmissive to allow a user to confirm the position of the donor tissue and/or carrier substrate 15.

Figure 22:
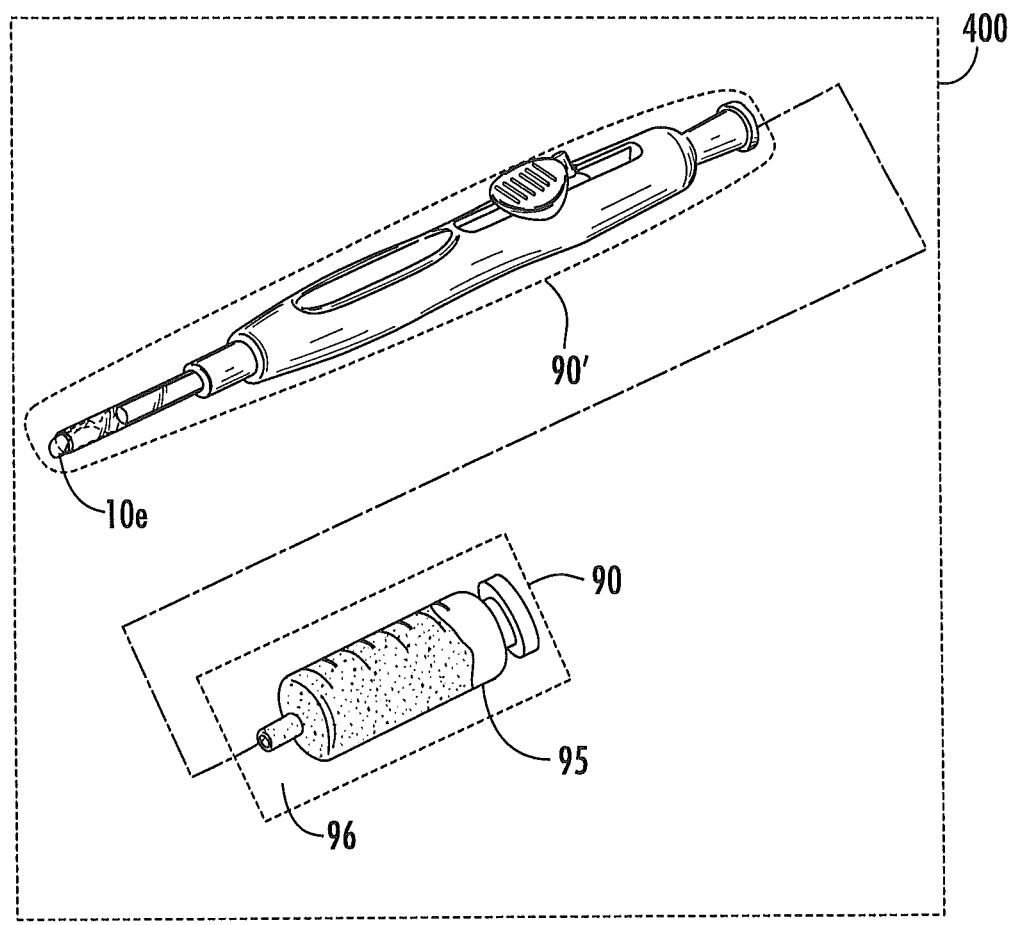
FIG. 22 is a schematic illustration of a medical kit according to embodiments of the present invention.

As shown in FIG. 20B, the tool 10 can also include a fluid delivery member 150 held with an end portion residing inside the first cannula 60 in communication (upstream but proximate to) with the implant material 25. The tool 10 can be configured to provide flow-through irrigation via the delivery member 150 that may be used to deploy tissue allograft and/or maintain chamber depth. In operation, the member 150 can be configured to remain substantially stationary both during initial loading of this carrier with tissue 25 into the cannula 60, and while the second cannula 65 and the first cannula 60 are axially retracted. The member 150 may be configured to facilitate the ejection of the tissue 25 from the tool 10. The member 150 may be configured to deliver pressurized fluid from the syringe 95 (FIG. 22). The member 150 can contact the tissue 25 directly and/or flowably direct fluid to contact the tissue 25. The member 150 can also deliver or push an intermediate fluid such as a gel (comprising, for example, a viscoelastic material) against a trailing edge of the tissue 25 to eject the tissue from the cannula 60 into a patient.

As shown in FIGS. 20A-20C, a proximal end portion of the device 10p may also comprise a luer lock 74 configured to releasably and sealably engage a syringe with sterile fluid (shown as feature 95 in FIG. 22). Sterile biocompatible fluid from the syringe 95 can be directed to flow through the device and exit the distal end portion of the device 10d. As noted above, the fluid can be used to deploy the target tissue, maintain chamber depth, and/or introduce supplemental target material to facilitate implantation, preparation and/or healing. The sterile biocompatible fluid may comprise gas and/or liquid. The syringe 95 can be used to flush the implant site prior to release of the target tissue delivery, and the fluid for this purpose typically comprises saline. The syringe 95 may also optionally be used to "prime" the fluid channel(s) extending in the tool 10 to employ the sterile fluid to eject air from the fluid irrigation channel(s) prior to surgical penetration in the target body region. The tool 10 can be configured to accept different fluids from different or the same syringe before or during the procedure. The syringe 95 can be configured to hold and deliver through the tool 10 a therapeutic fluid treatment. The luer lock 74 can be sealed closed prior to use to inhibit contamination (not shown). Similarly, a cap can be placed over the forward end of the tool 10e (also not shown).

In some particular embodiments, the tool 10 can provide a surgeon with substantially atraumatic donor corneal tissue handling and may promote precision placement of donor corneal allograft in a recipient's anterior chamber. The donor tissue can also be substantially atraumatically unsheathed in the recipient eye. As discussed above, the tool 10 can be single-use disposable.

FIG. 22 illustrates another embodiment of a medical kit 400. This medical kit 400 can comprise the tool 10 (loaded or unloaded with the donor tissue 25) and a biocompatible sterile 95 syringe. The syringe 95 can be configured with a male luer lock 96 sized and configured to matably engage with the female luer lock 74 on the tool 10. Each component may be held in sterile packaging 90.

Figure 23:
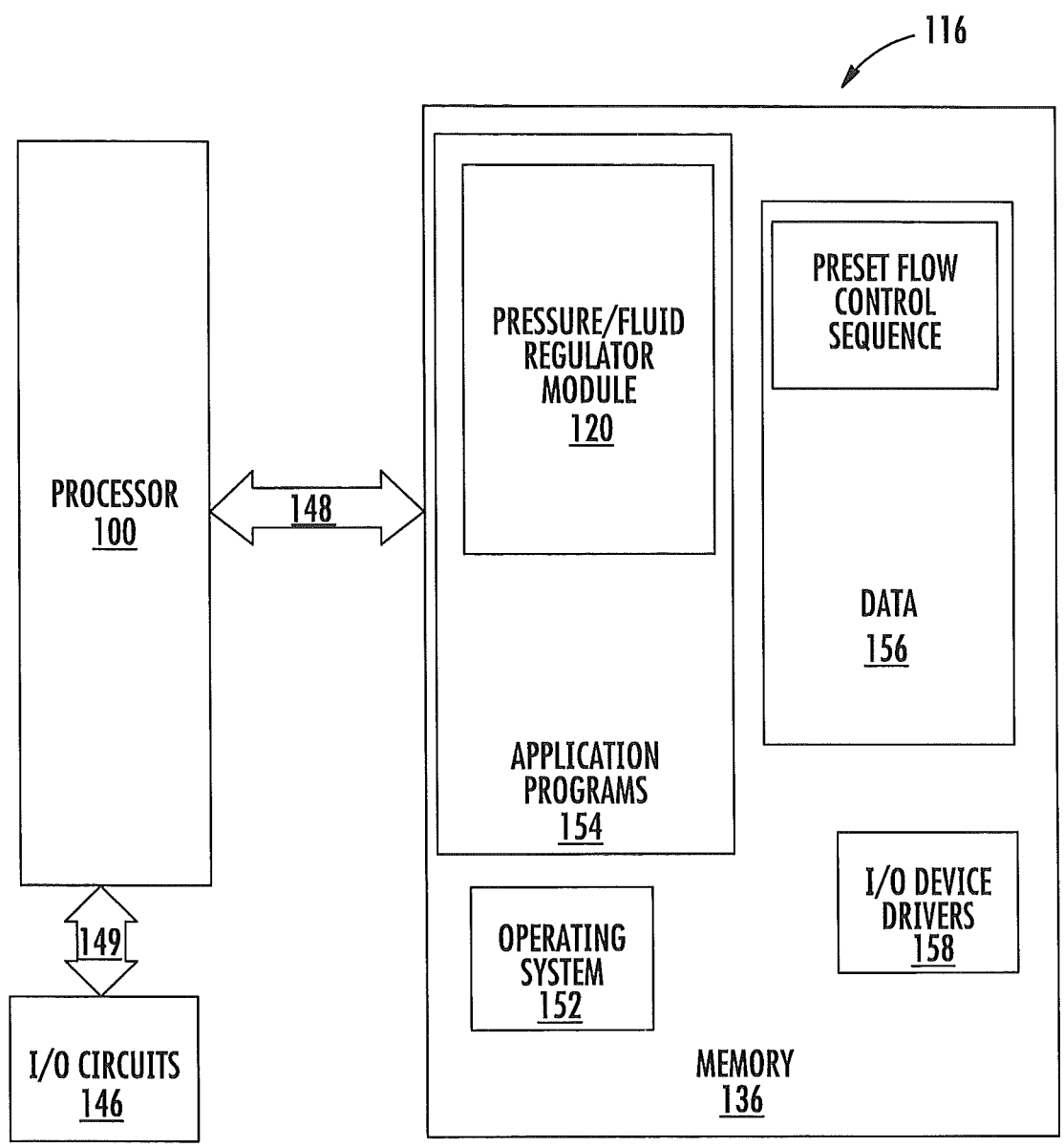
FIG. 23 is a diagram of a data processing system that can be used to electronically assist and/or control fluid pressure for delivery of the donor disc according to some embodiments of the present invention.

FIG. 23 illustrates a data processing system that may be used to control fluid delivery and/or plunger operation in some automated or semi-automated delivery systems. Thus, as will be appreciated by one of skill in the art, embodiments of the invention may be embodied as a method, system, data processing system, or computer program product. Accordingly, particular embodiments of the present invention may take the form of an entirely software embodiment or an embodiment combining software and hardware aspects, all generally referred to herein as a "circuit" or "module." Furthermore, certain particular embodiments of the present invention may take the form of a computer program product on a computer-usable storage medium having computer-usable program code embodied in the medium. Any suitable computer-readable medium may be utilized including hard disks, CD-ROMs, optical storage devices, a transmission media such as those supporting the Internet or an intranet, or magnetic or other electronic storage devices.

As such, computer program code for carrying out operations of the present invention may be written in an object oriented programming language such as Java, Smalltalk or C++. However, the computer program code for carrying out operations of the present invention may also be written in conventional procedural programming languages, such as the "C" programming language or in a visually oriented programming environment, such as VisualBasic.

Certain of the program code may execute entirely on one or more of the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). In some embodiments, some program code may execute on local computers and some program code may execute on one or more local and/or remote server. The communication can be done in real time or near real time or off-line using a volume data set provided from the imaging modality.

The invention is described in part herein with reference to flowchart illustrations and/or block diagrams of methods, systems, computer program products and data and/or system architecture structures according to embodiments of the invention. It will be understood that some blocks of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

As illustrated in FIG. 23, embodiments of the invention may be configured as a data processing system 116, which can be used to facilitate or carry out delivery of the disc 25, and can include a processor circuit 100, a memory 136 and input/output circuits 146. The data processing system may be incorporated in, for example, the tool 10 alone and/or one or more of a personal computer, workstation, server, router or the like. The processor 100 communicates with the memory 136 via an address/data bus 148 and communicates with the input/output circuits 146 via an address/data bus 149. The input/output circuits 146 can be used to transfer information between the memory (memory and/or storage media) 136 and another computer system or a network using, for example, an Internet protocol (IP) connection. These components may be conventional components such as those used in many conventional data processing systems, which may be configured to operate as described herein.

In particular, the processor 100 can be commercially available or custom microprocessor, microcontroller, digital signal processor or the like. The memory 136 may include any memory devices and/or storage media containing the software and data used to implement the functionality circuits or modules used in accordance with embodiments of the present invention. The memory 136 can include, but is not limited to, the following types of devices: ROM, PROM, EPROM, EEPROM, flash memory, SRAM, DRAM and magnetic disk. In some embodiments of the present invention, the memory 136 may be a content addressable memory (CAM).

As further illustrated in FIG. 23, the memory (and/or storage media) 136 may include several categories of software and data used in the data processing system: an operating system 152; application programs 154; input/output device drivers 158; and data 156. As will be appreciated by those of skill in the art, the operating system 152 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154 the operating system 152 the input/output device drivers 158 and other software programs that may reside in the memory 136.

The data 156 may include (electronically stored) predefined flow mode data sets 126, such as a pre-delivery flow and an active delivery flow of one or more flow pressures and/or flow rates. As further illustrated in FIG. 23, according to some embodiments of the present invention application programs 154 include a Flow Control or Fluid Regulator Module 120. The application program 120 may be located in a local server (or processor) and/or database or a remote server (or processor) and/or database, or combinations of local and remote databases and/or servers.

While the present invention is illustrated with reference to the application programs 154, 120 in FIG. 23, as will be also appreciated by those of skill in the art, other configurations fall within the scope of the present invention. For example, rather than being application programs 120, 154 these circuits and modules may also be incorporated into the operating system 152 or other such logical division of the data processing system. Furthermore, while the application program 120 is illustrated in a single data processing system, as will be appreciated by those of skill in the art, such functionality may be distributed across one or more data processing systems. Thus, the present invention should not be construed as limited to the configurations illustrated in FIG. 23, but may be provided by other arrangements and/or divisions of functions between data processing systems. For example, although FIG. 23 is illustrated as having various circuits and modules, one or more of these circuits or modules may be combined or separated without departing from the scope of the present invention.

As shown in FIG. 24A, as discussed with respect to FIGS. 19A and 19B, the medical tool 10 can have first and second cooperating elongate members 12, 14. The elongate members 12, 14 may have a length that is between about 6-15 mm, typically about 8-10 mm. As shown, the tool 10 receives a side edge portion of the disc 25 as shown in FIG. 24A. As shown in FIG. 24B, the distal edges of the members 12, 14 can be spaced apart by a distance 16 during the initial positioning. The distance 16 can be greater than the thickness of the donor disc 25. To provide for adequate separation and disc thickness variation, the distance 16 may be at least about 300 µm, typically between about 300-600 µm thick. However, other separation distances in the open configuration shown in FIGS. 24A and 24B may also be used. In this embodiment, the tool 10 can be described as a rolling tool 10 that rolls the disc 25 so that the lower donor stromal surface is on the outside surface 25e of the rolled body 25r (FIG. 28). In the embodiment shown in FIGS. 24A, 24B, no flexible substrate carrier is required. Also, the donor disc 25 can be rolled from a top edge portion toward a bottom edge portion. However, other rolled orientations can also be used (and the upper donor stroma may be on the outside of the rolled body).

As shown in FIGS. 25A and 25B, the elongate members 12, 14 also have a closed configuration whereby the members 12, 14 close to clamp or trap a side edge portion of the donor disc therebetween. In operation, a sleeve 30 can axially slide forward to force the members 12, 14 together. Typically, the members 12, 14 gently contact when in the closed configuration without the disc 25 therebetween as shown in FIG. 25B. FIGS. 26 and 27 illustrate that after the sleeve 30 is moved forward to close the members 12, 14 together with the side edge portion of the disc 25 therebetween, the tool 10 can be rotated one or more times to form the disc 25 into a rolled compact configuration as shown in FIG. 28. In this exemplary configuration, the disc 25 can have a rolled body 25r that has a length that is between about 8-8.25 mm and a width W (or height) of less than about 3 mm, typically about 2.5 mm.

During the rolling, the members 12, 14 are spaced apart and gently contact the disc 25 in a manner that allows the members 12, 14 to hold the disc 25 during rolling without imparting undue force on the endothelial cells to inhibit cellular injury.

Other tool configurations may be used to roll the disc into the desired configuration. For example, in some embodiments, an end cap or end clamp (not shown) can be used to force the members 12, 14 together (not shown). Similarly, the distal end of the tool may have a closed end rather than an end that can open and close, and the disk 25 can be inserted in between the two members 12, 14 (also not shown). It is also contemplated that a different roller tool configuration can be used, such as a single member (rather than cooperating spaced apart members) that can roll the disc (not shown). For example, a single member may cooperate with a separate tool or even manual manipulation until a first roll is started, and/or the tool may even employ a gentle biocompatible (liquid) adhesive.

Although the tool 10 is particularly suitable for rolling the disc 25, the tool 10 can be used to fold or otherwise hold the disc 25 as well. That is, it is contemplated that the tool 10 can fold the body of the disc with a lesser likelihood of endothelial damage compared to forceps where the force applied is less controlled. Indeed, the tool 10 may be used to hold the disc 25 in larger configurations for larger incision placement.

The elongate members 12, 14 can have a rounded cross-sectional shape and may have a smooth resilient contact surface, and may have a resilient body with sufficient rigidity to hold the disc during the rolling operations. The elongate members 12, 14 may comprise, for example, foam, sponge, cellulose, elastomer or polymer. The elongate members 12, 14 may also be formed of metal. The members 12, 14 may include surface coatings that inhibit slipping or provide lubricity to inhibit contact damage.

To promote reliability, efficiency and/or ease in surgical placement, it is contemplated that a standard rolled orientation will be used and/or that different medical kits noting the surgeon's desired rolled orientation can be provided. The latter can allow a surgeon to order a kit that is suitable for the particular entry incision used (which may vary depending on patient eye structure) and/or for a desired unrolling technique (side to side, top to bottom, bottom to top, offset, and the like). The rolled disc 25r may be configured for a temporal side or a superior entry. When unrolling in situ, rather than placing the rolled disc medially in the recipient stromal bed, the rolled disc 25r (FIG. 5) may be inserted closer to a side edge portion of the eye, the side edge portion typically being the one that corresponds to the last rolled portion. The donor disc can then be unrolled in an opposite direction using physical or fluid forces.

To promote increased efficiency in surgical procedures, an OEM or medical company can provide the donor disc 25 preformed in the rolled configuration 25*r* (FIG. 28) and ready for surgery. The rolled disc 25*r* may be held in a refrigerated storage condition prior to end use. The disc 25 may be rolled using different end use disc sizes and provided in a preformed rolled configuration for different end use sizes (about 8 mm and about 8.25 mm).

FIG. 29 illustrates that, in some embodiments, the rolling tool 10 can insert the rolled disc 25*r* into a discrete delivery device 250. In other embodiments, the tool 10 can hold the rolled disc 25*r* during implantation and hence, be the delivery device. As shown in FIG. 29, the delivery device 250 has a holding chamber 51 with a forward open portion 52; the forward portion 52 may have a beveled shape as shown. The chamber 51 is in fluid communication with a fluid source 75 (FIG. 31). The device 250 may also include a plunger 60.

In some embodiments, after the tool 10 enters the chamber 51, the sleeve 30 is retracted, thereby depositing the disc in the chamber 51. The tool 10 can be removed from the device 250. The tool 10 can be sterilized for re-use or be single-use disposable. As shown in FIG. 30, the rolled disc 25*r* is held in the chamber 51. The chamber 51 can have a width We that is between about 2.75 mm to about 5 mm, typically between about 3-4 mm wide, and in some embodiments about 3 mm wide. The chamber 51 has a length L sufficient to hold the length of the disc 25 therein, and is typically between about 8.5-10 mm long, typically about 9 mm long. Pressurized fluid can be introduced into the chamber 51 to urge or force the rolled disc 25*r* to exit the chamber 51. In some embodiments, as shown in FIG. 31, a perforated plunger 60 can be advanced to help expel the disc 25 from the chamber 51. The plunger 60 can allow fluid to enter the chamber through perforations or openings 66 in the plunger body. The fluid can comprise air, oxygen, saline, water or other suitable fluid. The openings 66 can be on the plunger head and/or via the arm 62. A different fluid can be introduced via the channel or opening in the arm 62. For example, air can be introduced through the arm 62 while a liquid can be introduced via side openings 66. Where a lubricant and/or viscoelastic substance (such as HEALON from Pharmacia in Nutley, N.J.) is used to preserve or protect the rolled disc 25*r*, a pre-delivery flushing may be desired to prepare the rolled disc 25*r* for surgical insertion (to remove at least some of the substance from the rolled disc 25*r* or chamber 51 prior to placement in the body).

The plunger 60 can be configured to allow a surgeon to manually advance the plunger 60 using the plunger arm 62, and the fluid source 75 may be directed to flow to the chamber 51 from a channel 53 that merges into the channel 63 in which the plunger arm 62 travels. FIG. 32A illustrates the device 250 with two paths 53, 63 and FIG. 32B illustrates the open end 52 of the device 250. This open end 52 may be capped or sealed prior to use to help seal the disc in a sterile environment.

In other embodiments, the plunger 60 can be configured to advance based on the pressurized fluid 75 and no separate plunger arm or plunger arm channel is required (not shown). In such a case, the channel 53 can be a straight channel (such as the plunger arm channel 63) to inhibit pressure drops. In any event, where a plunger 60 is employed, the plunger 60 may be configured to push indirectly, such as by pushing an intermediate fluid such as a gel (comprising, for example, a viscoelastic material) forward, thereby pushing the disc forward, or may directly (gently) contact the trailing edge of the rolled disc 25*r*.

Figure 36:
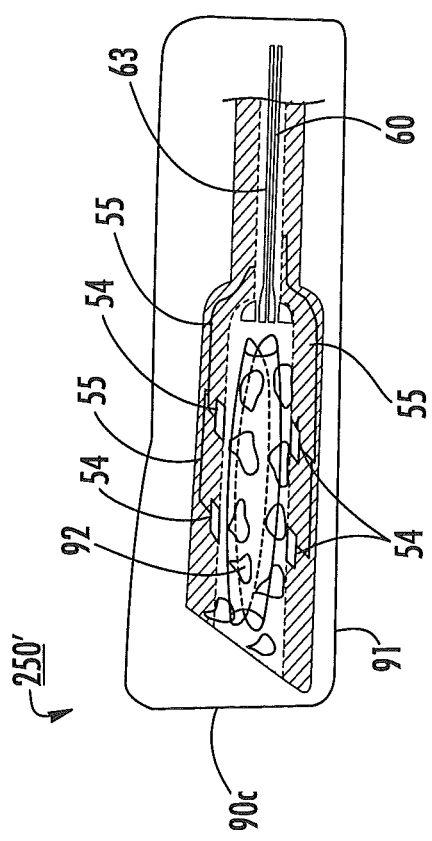
FIG. 36 is a schematic illustration of yet another medical kit with a rolled corneal donor disc with a holding chamber according to embodiments of the present invention.

FIG. 33 illustrates an exemplary surgical introduction of the device 250 to insert the rolled disc 25*r* into position in a recipient. As shown, fluid can be introduced into the chamber 51 and directed to flowably expel the rolled disc into position. The plunger 60 can be advanced to help expel the disc 25*r* as needed. FIG. 36 illustrates that the delivery device 250' can include a plurality of spaced apart flow orifices 54 (and may include micronozzles) that are configured to introduce fluid from a wall of the device into the chamber 51. The orifices 54 have an associated fluid channel 55 that can merge into the primary channel 63. The orifices 54 can reside axially and circumferentially spaced apart about the chamber 51 or may reside substantially aligned in a rearward portion of the chamber 51 to help initiate the expellant flow force onto the disc 25*r*. The orifices 54 may be configured as flushing ports that can expel pressurized fluid generally inward and axially forward. Alternatively, the orifices 54 can be configured to emit fluid under lesser pressures to inhibit adhesion to the chamber walls.

FIGS. 34-37 illustrate examples of preformed donor discs 25 provided as a medical product or kit 90. The reference number 90 is used to generally denote the medical product, but with respect to each embodiment in FIGS. 34-37, an alphabetical suffix is used to differentiate the specific product embodiment therein (i.e., 90*a*, 90*b*, 90*c*, 90*d*). The medical product 90 can be held in a sterile package 91. The package 90 can be a flexible package, such as an elastomeric- or foil-backed elastomeric package, or a rigid substrate package. Combinations of flexible and rigid packaging materials can also be used. A quantity of biocompatible liquid 92 can be placed about the disc 25 in the package 91. The liquid 92 can comprise sterile water, saline, viscoelastic material and the like.

Figure 34:
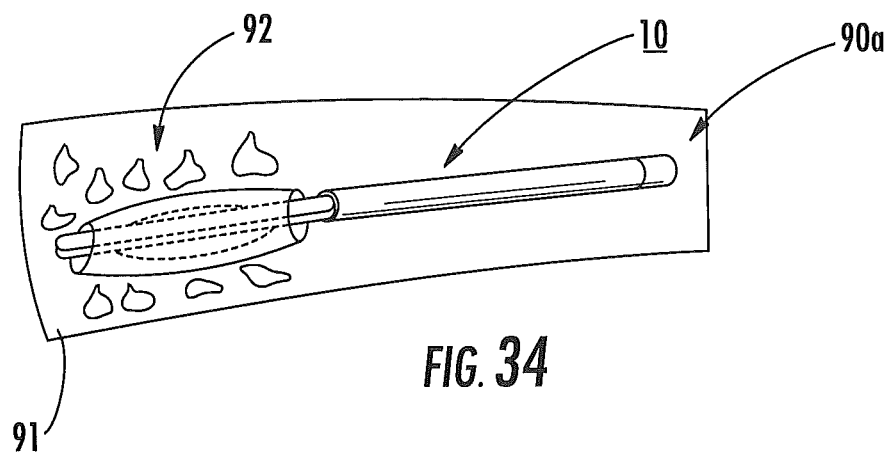
FIG. 34 is a schematic illustration of an exemplary medical kit with a rolled donor disc held by the rolling tool according to embodiments of the present invention.
Figure 35:
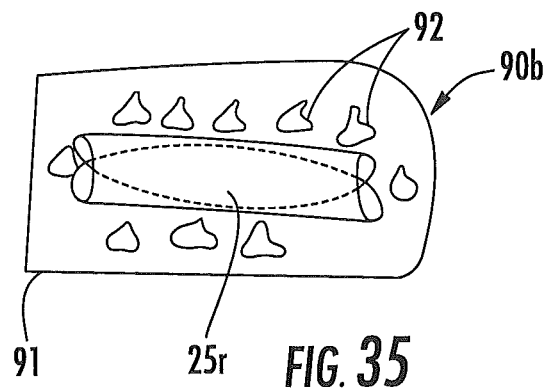
FIG. 35 is a schematic illustration of another exemplary medical kit with a rolled donor disc according to other embodiments of the present invention.
Figure 37:
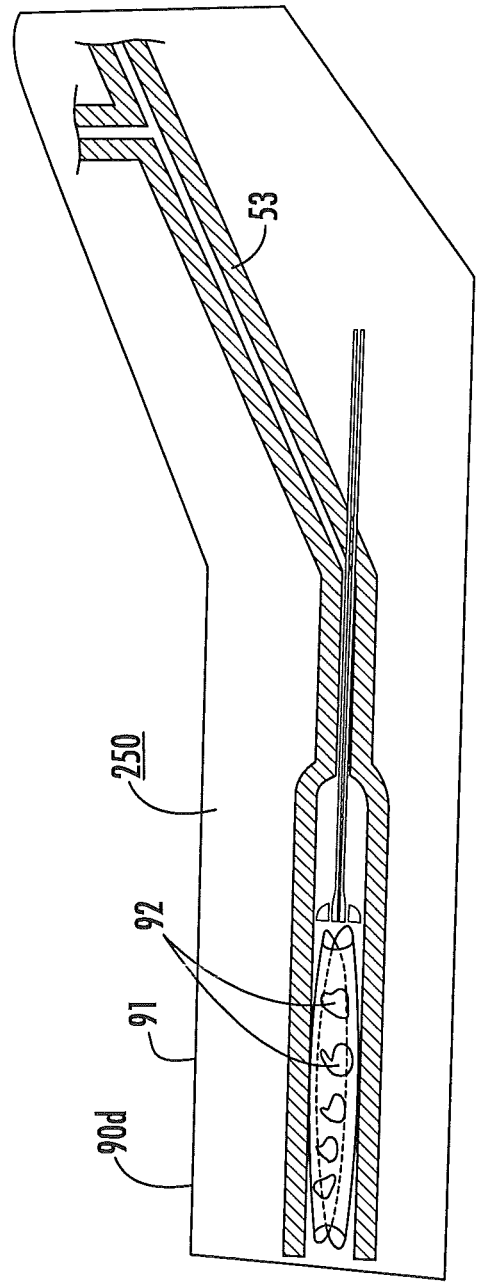
FIG. 37 is a schematic illustration of yet another medical kit with a rolled corneal donor disc and delivery system according to embodiments of the present invention.

FIG. 34 illustrates that the product 90*a* comprises a holding device (shown as the rolling tool itself) and the rolled disc 25*r*. FIG. 35 illustrates that the product 90*b* can be the rolled disc alone in the package 91. FIG. 36 illustrates that the product 90*c* can be a delivery tool 250 with the rolled disc 25*r* already in position therein. A fluid channel (conduit or other fluid channel configuration) can be provided as a separate tool in a kit or may be provided as standard components in a surgical suite. FIG. 37 illustrates the delivery device 250 and rolled disc 25*r* as well as a length of rigid flow pipe and/or flexible flow channel 53 that is configured to engage a pressurized fluid flow source (such as a syringe, a cylinder, or other flow source) at a surgical site.

In the product 90, the delivery device 250 and/or tool 10 can be labeled as single-use disposable. The portions of the product 90 that contact the body should be made from a biocompatible material and/or comprise a biocompatible coating.

The tool 10 and/or delivery device 250 (at least the forward body thereof) can comprise a sufficiently strong and relatively rigid elastomer, composite or ceramic or may comprise a metal, such as stainless steel. Combinations of these types of materials may also be used. In other embodiments, the tool members 12, 14 can be resiliently configured with sufficient structural rigidity to hold and form the rolled disc 25*r*.

FIG. 38 illustrates that the delivery device 250" may be resiliently compressible as represented by the arrows on each side of the device body. In operation, the outer wall 250*w* forming the chamber 51 can be compressed or pushed together to urge the disc 25*r* out of the chamber 51. In operation, a clinician can compress a rearward portion of the chamber 51 and work his or her way forward to squeeze or urge the disc out of the chamber. The device 250" may be configured to expel the disc 25*r* out and into position in the eye using only the compressibility of the walls, or the device 250" may be optionally configured to also employ a plunger and/or pressurized fluid as for the embodiments noted above. The device chamber 51 can be defined by a plasticized polymer or other suitable elastomeric material.

FIG. 39 illustrates that the rolling tool 10 or the delivery device 250''' (which can be used with any delivery device, such as embodiments 250, 250', 250") may be configured with visual alignment indicia 31, 151. The alignment indicia 31, 151 can comprise arrows, color or marked regions on an external viewable surface of the respective devices. For example, arrows or other indicia 31 on the sleeve 30 or forward portion of the body, such as a forward visible portion of members 12, 14, can help an operator insert the rolled disc 25r in a desired orientation into the chamber 51. This can facilitate reliable and proper positioning for enhanced operative positioning of the disc in the stromal bed. Similarly, visual indicia marking 151 on the delivery device 50''' can facilitate proper orientation with the incision cite and/or alignment with the tool 10 and/or 250. In other embodiments, no indicia is needed on the delivery device 250 as the configuration can be visibly unique (i.e., the top is visually different from a side or bottom portion) and the operator can align the indicia 31 with the target orientation of the delivery device, based on the configuration of the body.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A medical tool for implanting a tissue graft having an endothelial side in an eye of a patient, comprising:
   an elongate tubular body having opposing first and second end portions, the first end portion having a leading forward open end with a width that is between about 3 mm to about 6 mm, wherein the second end portion of the elongate body is configured to releasably engage a fluid source, and wherein the first end portion of the elongate body is configured to releasably hold the tissue graft in a rolled configuration;
   a tubular inner fluid delivery member in the elongate body configured to provide flow-through irrigation during implantation delivery of the tissue graft, wherein the tubular inner fluid delivery member is concentric with the leading forward open end of the elongate body;
   a flexible carrier substrate configured to be retracted to enter the tubular body while holding the tissue graft; and
   a control mechanism in communication with the flexible carrier substrate held over an outer surface of the elongate body that is configured to direct the flexible carrier to retract into the tubular body, wherein the flexible carrier substrate is configured to have a flat configuration outside the tubular body to hold the tissue graft thereon during loading and is configured to wrap about the tissue graft and automatically take on a rolled configuration with the rolled configuration of the tissue graft when retracted into the tubular body in response to movement of the control mechanism, and wherein
   during delivery, a user manually moves the control mechanism to cause the tool to release the tissue graft while fluid is emitted by the tubular inner fluid delivery member into an anterior chamber of the eye.

2. The medical tool of claim 1, wherein the flexible carrier substrate comprises one or more of an elastomer, polymer, copolymer or derivative thereof, and wherein the flexible carrier releasably conformably holds the tissue graft inside the tubular body with an endothelial side of the tissue graft facing away from the flexible carrier substrate.

3. The medical tool of claim 1, wherein, during delivery of the tissue graft into an anterior chamber of the eye of the patient, in response to movement of the control mechanism by a user, the tissue graft is atraumatically unsheathed from the tool while the flexible carrier substrate remains in the tool.

4. The medical tool of claim 2, wherein the flexible carrier substrate has a thin paddle portion that is flat outside the elongate body and has at least one aperture extending therethrough, the at least one aperture residing under or over a respective tissue graft.

5. The medical tool of claim 1, wherein a leading end of the tubular inner fluid delivery member is stationary and resides upstream of, but proximate, the tissue graft.

6. The medical tool of claim 1, wherein the first end portion of the tool includes at least one cannula slidably attached to a second cannula residing behind and concentrically aligned with the first cannula.

7. The medical tool of claim 1, wherein the elongate body has an externally accessible slot that engages a lock member that is in communication with the control mechanism to inhibit retraction of the first cannula, wherein the control mechanism slides longitudinally in the slot.

8. The medical tool of claim 1, wherein the leading forward open end is tapered.

9. The medical tool of claim 1, wherein the second end portion of the tool body comprises a luer lock that releasably engages the fluid source.

10. The medical tool of claim 9, wherein the fluid source comprises a syringe of biocompatible sterile fluid that is sized and configured to releasably engage the luer lock.

11. The medical tool of claim 1, further comprising a tissue graft held inside the first end portion of the elongate body, wherein the tissue graft is a donor corneal grafting disc having a diameter between about 8-8.25 mm and a thickness between about 100-200 μm for small incision endothelial keraloplasty.

12. The medical tool of claim 1, wherein at least a portion of the first cannula is visually transmissive.

13. A method of configuring an endothelial donor corneal disc for transplantation, comprising:
   providing a corneal transplantation donor tissue graft;
   placing the corneal transplantation donor tissue graft in an injector having a leading open end and an inner tubular fluid delivery member that is concentric with the leading open end of the injector, wherein the donor tissue graft has a rolled configuration inside the injector;
   attaching a container of irrigant fluid to the injector to be in fluid communication with the inner tubular fluid delivery member;
   inserting the leading open end of the injector in an eye of a patient; then
   sliding a manual slide control button to a deploy position to deliver the corneal transplantation donor tissue graft in an anterior chamber of the eye; and
   flowing irrigant out of the inner tubular fluid delivery member and into the anterior chamber of the eye during delivery of the corneal transplantation donor tissue graft.

14. The method of claim 13, wherein the placing the corneal transplantation donor tissue graft in the injector is carried out by:

placing the corneal transplantation donor tissue graft on a planar thin flexible substrate; then slidably retracting the thin flexible substrate with the corneal transplantation donor tissue graft inside the injector; and rolling the flexible substrate with the corneal transplantation donor tissue graft into the rolled configuration as the flexible substrate with the corneal transplantation donor tissue graft slidably enter the injector in response to the slidably retracting step.

15. The method of claim 14, wherein the sliding the manual slide control button is carried out so that the flexible substrate remains in the injector during placement of the corneal transplantation donor tissue graft in the anterior chamber of the eye.

16. The method of claim 14, wherein the rolling comprises forcing opposing outer edges to reside proximate each other over an axially extending medial portion thereof without forming sharp fold edges or creases.

17. The method of claim 13, wherein the corneal transplantation donor tissue graft has an endothelial side and an opposing stromal side, and wherein, before sliding the manual slide control to a deploy position, a user rotates the injector so that the stromal side is facing upward and the endothelial side is facing downward for placement in the anterior chamber.

18. The method of claim 13, wherein the corneal transplantation donor tissue graft is a donor disk with a diameter between about 8 mm to about 9 mm, and wherein the rolled disk inside the injector has a cross-sectional width of about 3 mm suitable for entering a scleral access incision sized at less than about 4 mm.

19. A medical tool, comprising:

a flexible platform;

a barrel having a tapered end slidably holding the flexible platform, the tapered end sized and configured to transfer endothelial cell tissue through a small incision into an anterior chamber of a patient's eye substantially without endothelial cell trauma, wherein the tapered end of the barrel defines a cavity with a leading open end having a width that is between about 3 mm to about 6 mm;

a control member that is in communication with the platform and held by the barrel to slidably advance and retract the platform in and out of the barrel; and a fluid source in fluid communication with the barrel, wherein the tapered end of the barrel is configured to coaxially deliver fluid from the tapered end to maintain an anterior chamber of the patient's eye during transfer of the implant tissue, wherein the flexible platform has a flat shape outside the barrel and is configured to automatically take on a different rolled shape as the flexible platform enters the tapered end of the barrel, wherein, to load the cell tissue, a user moves the control member to retract the platform into the barrel with the endothelial cell tissue and the platform with the cell tissue are formed into a substantially cylindrical shape while the platform holds the cell tissue on a primary surface thereof.

* * * * *

UNITED STATES PATENT AND TRADEMARK OFFICE
CERTIFICATE OF CORRECTION

PATENT NO. : 8,673,002 B2  
APPLICATION NO. : 13/901115  
DATED : March 18, 2014  
INVENTOR(S) : Walter et al.

Page 1 of 1

It is certified that error appears in the above-identified patent and that said Letters Patent is hereby corrected as shown below:

On Title Page:  
Item 73, Assignee:  
Please correct "Wake Forest University Health Science, Winston-Salem, NC (US)"  
    to read -- Wake Forest University Health Sciences, Winston-Salem, NC (US) --

Signed and Sealed this  
Thirteenth Day of January, 2015

Michelle K. Lee  
*Deputy Director of the United States Patent and Trademark Office*